US009493787B2

(12) United States Patent
Diergaarde et al.

(10) Patent No.: US 9,493,787 B2
(45) **Date of Patent: *Nov. 15, 2016**

(54) **POWDERY MILDEW RESISTANCE PROVIDING GENES IN *CUCUMIS SATIVUS***

(75) Inventors: Paul Johan Diergaarde, Amersfoort (NL); Leonora Johanna Gertruda Van Enckevort, Wageningen (NL); Karin Ingeborg Posthuma, Enkhuizen (NL); Marinus Willem Prins, Amersfoort (NL)

(73) Assignees: Enza Zaden Beheer B.V., Enkhuizen (NL); Keygene N.V., Wageningen (NL)

( * ) Notice: Subject to any disclaimer, the term of this patent is extended or adjusted under 35 U.S.C. 154(b) by 159 days.

This patent is subject to a terminal disclaimer.

(21) Appl. No.: 14/002,284

(22) PCT Filed: Feb. 20, 2012

(86) PCT No.: PCT/EP2012/052843

§ 371 (c)(1), (2), (4) Date: Oct. 29, 2013

(87) PCT Pub. No.: WO2013/017293

PCT Pub. Date: Feb. 7, 2013

(65) Prior Publication Data

US 2014/0157454 A1 Jun. 5, 2014

(30) Foreign Application Priority Data

Mar. 1, 2011 (WO) ................. PCT/EP2011/053054

(51) Int. Cl.

*C12N 15/82* (2006.01)
*C07K 14/41* (2006.01)
*C07K 14/415* (2006.01)

(52) U.S. Cl.

CPC ......... *C12N 15/8282* (2013.01); *C07K 14/415* (2013.01)

(58) Field of Classification Search

None
See application file for complete search history.

(56) References Cited

FOREIGN PATENT DOCUMENTS

| | | |
|---|---|---|
| WO | 9804586 A2 | 2/1998 |
| WO | 2008017706 A1 | 2/2008 |

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*

Guo et al (Protein tolerance to random amino acid change, Proc. Natl. Acad. Sci. USA 101:9205-9210, 2004).*

Huang et al (The genome of the cucumber, *Cucumis sativus* L. Nature Genetics. 41: 1275-1283, 2009).*

Panstruga (Discovery of novel conserved peptide domains by ortholog comparison within plant multi-protein families. Plant Molecular Biology 59:485-500, 2005).*

Xin et al (Diverse set of microRNAs are responsive to powdery mildew infection and heat stress in wheat (*Triticum aestivum* L.) BMC Plant Biology.10:123, 2010).*

Cheng et al., "Molecular cloning and expression analysis of CmMlo1 in melon," Mol Biol Rep, vol. 39, 2012, Published online Jun. 10, 2011, pp. 1903-1907.

Panstruga, "Discovery of novel conserved peptide domains by ortholog comparison within plant multi-protein families," Plant Molecular Biology, vol. 59, 2005, pp. 485-500.

Panstruga, "Serpentine plant MLO proteins as entry portals for powdery mildew fungi," Biochemical Society Transactions, vol. 33, Part 2, 2005, pp. 389-392.

Schweizer et al., "Double-stranded RNA interferes with gene function at the single-cell level in cereals," The Plant Journal, vol. 24, No. 6, 2000, pp. 895-903.

* cited by examiner

*Primary Examiner* — Medina A Ibrahim
*Assistant Examiner* — Wayne Zhong
(74) *Attorney, Agent, or Firm* — The Webb Law Firm

(57) ABSTRACT

The present invention relates to powdery mildew resistance providing genes of the *Cucumis* family, and especially *Cucumis sativus*, wherein said resistance is provided by impairment of the present genes. Further, the present invention relates plants comprising the present impaired resistance conferring genes and seeds, embryos or other propagation material thereof. Especially, the present invention relates to powdery mildew resistance conferring genes, wherein the amino acid sequence encoded by said resistance conferring gene is selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 and SEQ ID No. 22, and amino acid sequences with more than 70% identity, preferably more than 80% identity, more preferably more than 90% identity, and most preferably more than 95% identity.

15 Claims, 4 Drawing Sheets

```
  1 CCCGCAATGTGGCTATTTGCTGTTCTCTTCATCCTAACCAATACAAATGGGTGGTATTCATATC 64
    ||||||||||||||||||||||||||||||||||||||||||||||||||||||||||||||||
    CCCGCAATGTGGCTATTTGCTGTTCTCTTCATCCTAACCAATACAAATGGGTGGTATTCATATC

 65 TATGGCTGCCTTTCATCTCCTTAATTATAATTCTATTGGTGGGAACAAAGCTCCATGTTATTAA 128
    |||||||||||||||||||||||||||||||||||||||
    TATGGCTGCCTTTCATCTCCTTAATTATAATTCTATTGG-------------------------

129 AACTCATATGGGATTGACAATTCAAGAAAGGGGTCATGTTGTGAAGGGTGTTCCGGTCGTTCAC 192
                                                    ||||||||||||||||
    ------------------------------------------------GTGTTCCGGTCGTTCAG

193 GCTCGGG 199
    |||||||
    CCTCGGG
```

POWDERY MILDEW RESISTANCE PROVIDING GENES IN *CUCUMIS SATIVUS*

CROSS-REFERENCE TO RELATED APPLICATIONS

This application is the United States national phase of International Application No. PCT/EP2012/052843 filed Feb. 20, 2012, and claims priority to International Application No. PCT/EP2011/053054, filed Mar. 1, 2011, the disclosures of which are hereby incorporated by reference in their entirety.

BACKGROUND OF THE INVENTION

Field of the Invention

The Sequence Listing associated with this application is filed in electronic format via EFS-Web and is hereby incorporated by reference into the specification in its entirety. The name of the text file containing the Sequence Listing is 133292_ST25.txt. The size of the text file is 109,616 bytes, and the text file was created on Feb. 6, 2014.

The present invention relates to powdery mildew resistance providing genes of *Cucumis sativus*, wherein said resistance is provided by impairment of the present genes either at the expression or protein level. Further, the present invention relates to plants comprising the present resistance conferring genes and seeds, embryos or other propagation material thereof.

Powdery mildew (PM) is one of the main fungal diseases known in plants belonging to the *Cucumis* family such as *Cucumis sativus* (cucumber), both in the field and greenhouse.

Powdery mildew diseases are generally caused by many different species of fungi of the order *Erysiphales*. The disease is characterized by distinctive symptoms such as white powder-like spots on the leaves and stems. Generally, the lower leaves are the most affected, but the mildew can appear on any part of the plant that is exposed above ground. As the disease progresses, the spots get larger and thicker as massive numbers of spores form, and the mildew spreads up and down the length of the plant such as on the stem and even the fruits.

Severely affected leaves can become dry and brittle, or can wither and die. Because of the infection, the fruits can be smaller in size, fewer in number, less able to be successfully stored, sun scalded, incompletely ripe, and having a poor flavor. It may also predispose plants to be more vulnerable to other pathogens. Eventually, the plant can die.

Powdery mildew can, amongst others, be caused by the fungus *Sphaerotheca fuliginea* (recently renamed: *Podosphaera xanthii* also designated as *Oidium erysiphoides*) and/or *Erysiphe cichoracearum* DC (recently renamed: *Golovinomyces cichoracearum* also designated as *Oidium chrysanthemi*).

Considering the economic importance of *Cucumis* plant species, such as cucumber, there is a continued need in the art to provide powdery mildew resistance providing genes.

In view of the above need in the art, it is an object of the present invention, amongst other objects, to meet this need.

SUMMARY OF THE INVENTION

According to the present invention, this object, amongst other objects, is met by a powdery mildew resistance conferring gene as defined in the appended claim 1.

Specifically, this object of the present invention, amongst other objects, is met by a powdery mildew resistance conferring gene, wherein the amino acid sequence encoded by said resistance conferring gene is selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 and SEQ ID No. 22, and amino acid sequences with more than 70% identity, preferably more than 80% identity, more preferably more than 90% identity, and most preferably more than 95% identity such as more than 96%, 97%, 98%, 99%; and wherein said resistance conferring gene is impaired.

The object of the present invention, amongst other objects, is additionally met by a powdery mildew resistance conferring gene, wherein the cDNA sequence transcribed from said resistance conferring gene is selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, and SEQ ID No. 21, and cDNA sequences with more than 70% identity, preferably more than 80% identity, more preferably more than 90% identity, and most preferably more than 95% identity such as more than 96%, 97%, 98%, 99%; and wherein said resistance conferring gene is impaired.

BRIEF DESCRIPTION OF THE DRAWINGS

FIG. 2: shows DNA fragments of CsKIP2 amplified with primers ID3 (SEQ ID NO: 25) and ID4 (SEQ ID NO: 26) and visualized by gel electrophoresis (2% agarose, 10 v/cm, 40 minutes).

FIG. 3: shows cDNA sequence alignment of lines with absence (top strand, SEQ ID NO: 27) and presence (bottom strand, SEQ ID NO: 27) and presence (bottom strand) of a transposon-like element in CsKIP2 genomic DNA. Here, a 72 by deletion is visible in cDNA derived from lines with the transposon-like element present. Primer binding positions are shown in bold italic characters.

Figure 1:
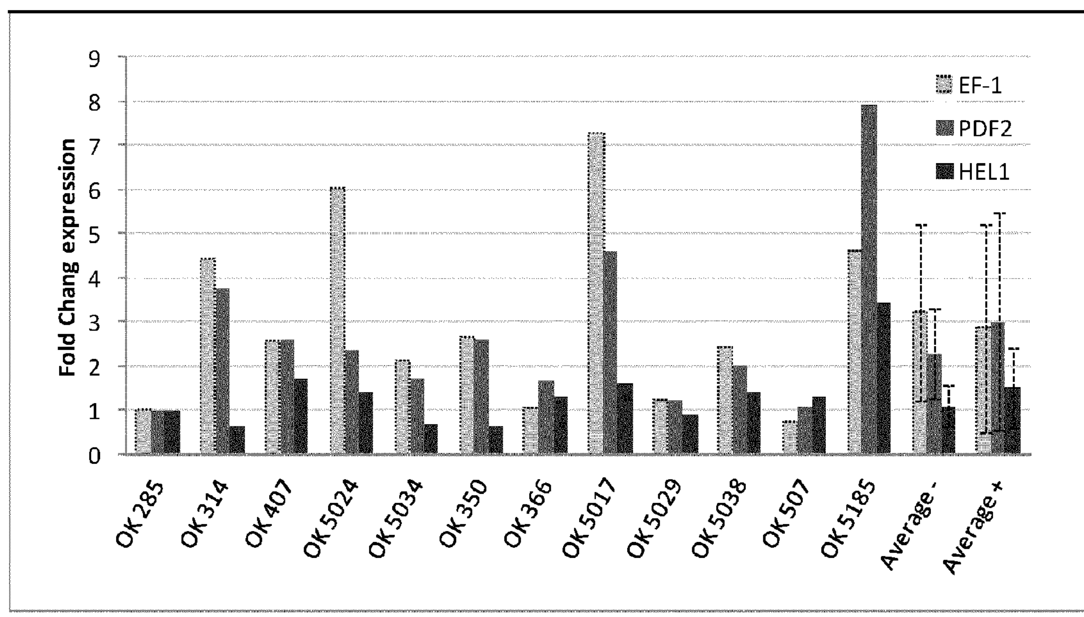
FIG. 1: shows Relative expression levels of CsKIP2 in a selection of cucumber germplasm. Average values of expression per group either in absence (−) or presence (+) of a transposon are added including standard deviation error bars. Bar colors indicate the reference gene used to make the calculations.

| | |
|---|---|
| CsMlo9OK561 | SEQ ID No: 29 |
| CsMlo9OK537 | SEQ ID No: 30 |
| CsMlo9OK619 | SEQ ID No: 31 |
| CsMlo9OK123 | SEQ ID No: 32 |
| CsMlo9OK563 | SEQ ID No: 33 |
| Consensus | SEQ ID No: 34 |

DESCRIPTION OF THE INVENTION

Impaired resistance conferring gene according to the present invention is meant to indicate a gene providing a reduced, or even absent, susceptibility to powdery mildew caused by fungi indicated by powder-like spots on the leaves and stems, such as fungi belonging to the order *Erysiphales* such as *Sphaerotheca fuliginea* (recently renamed:

*Podosphaera xanthii* also designated as *Oidium erysiphoides*) and/or *Erysiphe cichoracearum* DC.

Impaired resistance conferring gene-genes according to the present invention are mutated genes. The mutation of the present genes can, through different mechanisms, result in impairment. For example, mutations in protein encoding DNA sequences may lead to mutated, truncated or non-functional proteins. Mutations in non-coding DNA sequences may cause alternative splicing, translation or protein trafficking. Alternatively, a mutation resulting in an altered transcriptional activity of a gene, which determines the amount of mRNA available for translation to protein, may result in low levels, or absence, of proteins. Additionally, the impairment of gene function may be caused after translation, i.e. at protein level.

Impairment according to the present invention is also indicated by observing a powdery mildew resistance in a *Cucumis sativus* plant comprising a gene which as mutated at the protein level as compared to the SEQ ID Nos. provided herein or no expression of the SEQ ID Nos. provided herein is observed.

Impaired is also indicated herein as a nonfunctional gene or protein. Although the function of the present genes is not yet identified, a non-functional gene or protein can be readily determined by establishing powdery mildew resistance (non-functional) or powdery mildew susceptibility (functional) in a plant. A powdery mildew resistance (non-functional) plant is indicated by comprising a gene which as mutated at the protein level as compared to the SEQ ID Nos. provided herein or no expression of the SEQ ID Nos. provided herein is observed.

Functional and non-functional genes or proteins can also be determined using complementation experiments. For example, transforming a resistant powdery mildew *Cucumis sativus* plant with any of the present genes or proteins will result in a powdery mildew susceptible *Cucumis sativus* plant when the gene or protein is functional while the *Cucumis sativus* plant will remain resistant when the gene or protein is non-functional.

According to the present invention, the present powdery mildew resistance conferring genes provide powdery mildew resistance when the present genes are impaired. Impaired according to the present invention can be indicated by the absence, or decrease of a functional, or non-muted, protein identified herein as SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 or SEQ ID No. 22. In the art, many mechanisms are known resulting in the impairment of a gene either at the transcription, translation or protein level.

For example, impairment at the transcription level can be the result of one or more mutations in transcription regulation sequences, such as promoters, enhancers, and initiation, termination or intron splicing sequences. These sequences are generally located 5' of, 3' of, or within the coding sequence represented by SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, or SEQ ID No. 21. Impairment can also be provided by a deletion, rearrangement or insertion in the present genes.

Impairment at the translation level can be provided by a premature stop-codons or other RNA→protein controlling mechanisms (such as splicing) or posttranslational modifications influencing, for example, protein folding or cellular trafficking.

Impairment at the protein level can be provided by truncated, misfolded or disturbed protein-protein interactions.

Independent of the underlying mechanism, impairment according to the present invention is indicated by a decrease or absence of a functional protein according to SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 or SEQ ID No. 22.

According to a preferred embodiment, impairment according to the present invention is provided by one or more mutations in the present genes resulting in the absence of a protein expression product. As indicated, these mutations can cause a defective expression at the transcription or translation level.

According to another preferred embodiment, impairment according to the present invention is caused by one or more mutations in the present genes resulting in a non-functional protein expression product. A non-functional protein expression product can, for example, be caused by premature stop-codons, incorrect translation or posttranslational processing or by insertions, deletions or amino acid changes.

Using molecular biology methods, impairment of the present genes can also be accomplished by gene silencing, for example using siRNA or knocking out of the present genes. Methods based on EMS or other mutagenic chemical compounds capable of randomly changing nucleic acids into other nucleotides are also contemplated within the context of the present invention. Detection of such mutations typically involves high sensitivity melting curve analyses or nucleotide sequencing-based TILLING procedures.

The present invention relates to nucleotide and amino acid sequences with more than 70%, preferably more than 80%, more preferably more than 90% and most preferably more than 95% sequence identity either at the nucleotide level or the amino acid level.

Sequence identity as used herein is defined as the number of identical consecutive aligned nucleotides, or amino acids, over the full length of the present sequences divided by the number of nucleotides, or amino acids, of the full length of the present sequences and multiplied by 100%.

For example, a sequence with 80% identity to SEQ ID No. 1 comprises over the total length of 1782 nucleotides of SEQ ID No. 15 1426 identical aligned consecutive nucleotides, i.e., 1426/1782*100%=80%.

According to the invention, the present genes are derived from *Cucumis sativus*.

According to another aspect, the present invention relates to *Cucumis sativus* plants comprising in their genome the present impaired powdery mildew resistance conferring genes, i.e., plants not expressing a functional protein selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 and SEQ ID No. 22, and amino acid sequences with more than 70% identity, preferably more than 80% identity, more preferably more than 90% identity, and most preferably more than 95% identity.

In general, and preferably, the present plants will be homozygous for the present impaired genes, i.e., comprising two impaired powdery mildew resistance conferring genes, wherein the cDNA sequence transcribed from said resistance conferring gene is selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, and SEQ ID No. 21, and cDNA sequences with more than 70% identity, preferably more than 80% identity, more preferably more than 90% identity, and most preferably more than 95% identity.

Considering the benefits of the present plants, i.e., providing powdery mildew resistance in cucumber plants, the invention also relates to seeds, plant parts or propagation material capable of providing the present powdery mildew resistant cucumber plants which seeds, plant parts or propagation material comprise one or more of the present powdery mildew resistance conferring genes, i.e., impaired powdery mildew resistance conferring genes, wherein the cDNA sequence transcribed from said resistance conferring gene is selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, and SEQ ID No. 21, and cDNA sequences with more than 70% identity, preferably more than 80% identity, more preferably more than 90% identity, and most preferably more than 95% identity.

According to yet another aspect, the present invention relates to isolated nucleotide sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, and SEQ ID No. 21, and nucleotide sequences with more than 70% identity, preferably more than 80% identity, more preferably more than 90% identity, and most preferably more than 95% identity.

According to still another aspect, the present invention relates to isolated amino acid sequences selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 and SEQ ID No. 22, and amino acid sequences with more than 70% identity, preferably more than 80% identity, more preferably more than 90% identity, and most preferably more than 95% identity.

The present invention also relates to the use of one or more of the present powdery mildew resistance conferring genes, one or more of the present isolated nucleotide sequences, or one or more of the present isolated amino acid sequences for providing a powdery mildew resistant cucumber plant (*Cucumis sativus*). As indicated, the present use is based on impairment, either at the expression or protein level, of the genes described herein and can be readily determined by the presently provided cDNA and amino acid sequences optionally in combination with determination of the presence or absence of powdery mildew resistance and/or in combination with complementation assays.

The present invention will be further described in the examples below of preferred embodiments of the present invention. In the example, reference is made to figures wherein:

EXAMPLES

Example 1

Cucumber Germplasm Screen for Contribution of CsKIP2 Expression Levels and Allelic Variants to Resistance/Susceptibility Introduction Impairment of functioning of genes can be caused by different mechanisms. Mutations in protein encoding DNA sequences may be causal for loss-of-function alleles or genes with a change in characteristics. Alternatively, altered transcriptional activity of a gene, which determines the amount of mRNA available for translation to protein, may result in low levels of available proteins. Additionally, the impairment of gene function may be caused after translation, i.e. at protein level.

The present example shows that a mutation (deletion) in the coding sequence of CsKIP2 provides powdery mildew resistance.

Material and Methods

A total of twelve Cucumber germplasm lines varying in powdery mildew resistance levels were selected for analysis. Seeds were germinated under standard greenhouse conditions. Hypocotyls were infected with a local powdery mildew isolate 7 days past sowing followed by infection of the first true leaf 14 days past sowing. Evaluation of reaction phenotypes was performed 28 days past sowing (21 and 14 days post infection for hypocotyls) and phenotypes are scored on a scale of 1-9, where 1 is fully susceptible and 9 is fully resistant.

Material of infected plants was collected for subsequent RNA isolation according to standard procedures (Machery-Nagel RNA Plant). RNA isolation was followed by cDNA synthesis using a standard Oligo-dT primer combined with a reverse transcriptase (Finnzymes) with 1 μg total RNA input.

Expression levels of CsKIP2 were determined with CsKIP2 specific PCR primer pair (table 1, ID1 ID2) amplifying a DNA fragment from exon 5 to exon 7 with a size specific to cDNA, highly different of the product size derived from genomic DNA. In addition, control fragments functioning as internal reference were amplified from three different housekeeping genes i.e. Elongation Factor 1-alpha (EF-1, *A. thaliana* ortholog At1g07920.1), Protein Phosphatase 2a subunit a2 (PDF2, *A. thaliana* ortholog At3g25800.1) and Helicase domain containing protein 1 (HEL1, *A. thaliana* ortholog At1g58050.1).

For specific real time detection of dsDNA during PCR amplification, LCGreen (Idaho Technologies) was added to the PCR reaction mixture at 0.5× concentration. Calculations were made using the ΔΔCt method.

For the detection of allelic variants with CsKIP2, a specific region was targeted in the cDNA. This region is suspected to house a transposon-like element (exon 11 transposon). Primers (table 1, ID3 ID4)) designed to specifically amplify exon 9 (partial), 10 and 11 (partial) of CsKIP2 were used for the detection of this fragment.

TABLE 1

| CsKIP2 specific PCR primers | |
|---|---|
| ID1: 5' CGACACTTGAGCTTCTGGAG 3' | SEQ ID NO. 23 |
| ID2: 5' GCAAGATGTGCAACAATGAATC 3' | SEQ ID NO. 24 |
| ID3: 5' CCCGCAATGTGGCTATTTGCTGT 3' | SEQ ID NO. 25 |
| ID4: 5' CCCGAGGCTGAACGACCGGA 3' | SEQ ID NO. 26 |

Results

A selection of 12 germplasm lines from the powdery mildew disease test was made for subsequent expression studies and detection of allelic variation of CsKIP2. Presence or absence of a transposon-like element suspected to be the causative factor of powdery mildew resistance in genomic DNA was done before starting expression studies in order to investigate its effect on expression.

Expression of CsKIP2 in leaf material derived from the selected plants was determined based on the control genes. The results show no general effect of expression based on the obtained data. On average, expression levels observed are similar (FIG. 1)

Figure 2:
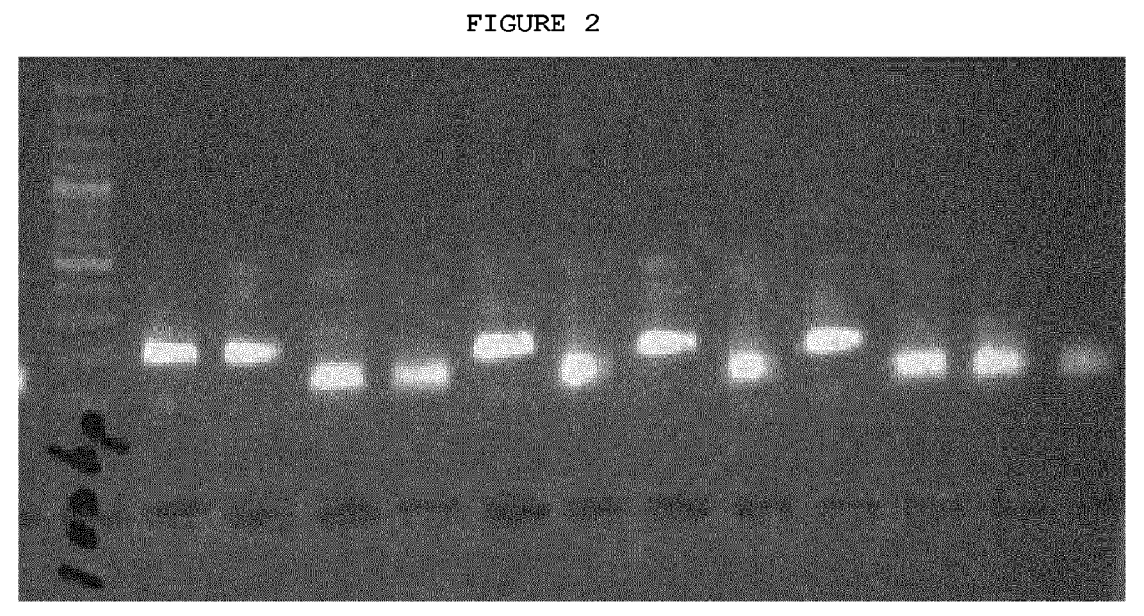

After determination of expression levels, the allelic variation in the transposon-like element was investigated. The fragment amplified with primers ID3 and ID4 produced a variable fragment of size 199 by or 127 bp (FIG. 2). The smaller fragment was found strictly in resistant plants and correlates to the presence of the transposon in genomic DNA.

The sequence of the fragments was found to be highly similar except for a 72 bp deletion in exon 11, centered around the original position of the transposon in genomic DNA (FIG. 3).

Conclusions

Expression analysis of CsKIP2 in leaf material from infected cucumber plants was carried out in order to assess the involvement of gene expression in resistance. On average, expression levels were similar in resistant and susceptible plants.

The presence of a transposon-like element found in exon 11 of the CsKIP2 gene in genomic DNA was also found not to be correlated to expression levels of CsKIP2.

The presence of the transposon-like element in genomic DNA was found to be related to resistance of plants to powdery mildew. The resistant plants with the transposon-like element in the genomic DNA showed a deletion of 72 bp in exon 11 in the cDNA, compared to susceptible plants.

Apparently, the mechanism responsible for the correct splicing of RNA (i.e. separating exons from introns), splices the transposon-like element from the RNA, along with a part (i.e. 72 bp) of the coding sequence. After translation of mRNA to protein, the 72 bp deletion mRNA results in a protein with a 24 amino acid residue deletion. The 24 amino acid residue deletion protein product (i.e. CsKIP2 from resistant plants) is believed to have lost its function as host-factor.

Example 2

Cucumber Germplasm Screen for Contribution of CsKIP9 Allelic Variants to Resistance/Susceptibility The cDNA sequence of CsKIP9 of 5 cucumber plants was determined. Table 2 below summarizes the plant plants tested and their powdery mildew resistance.

TABLE 2

| Cucumber plants | Powdery mildew resistant | SEQ ID No. |
|---|---|---|
| OK561 | – | 29 |
| OK537 | + | 30 |
| OK619 | + | 31 |
| OK123 | + | 32 |
| OK563 | – | 33 |

Figure 4:
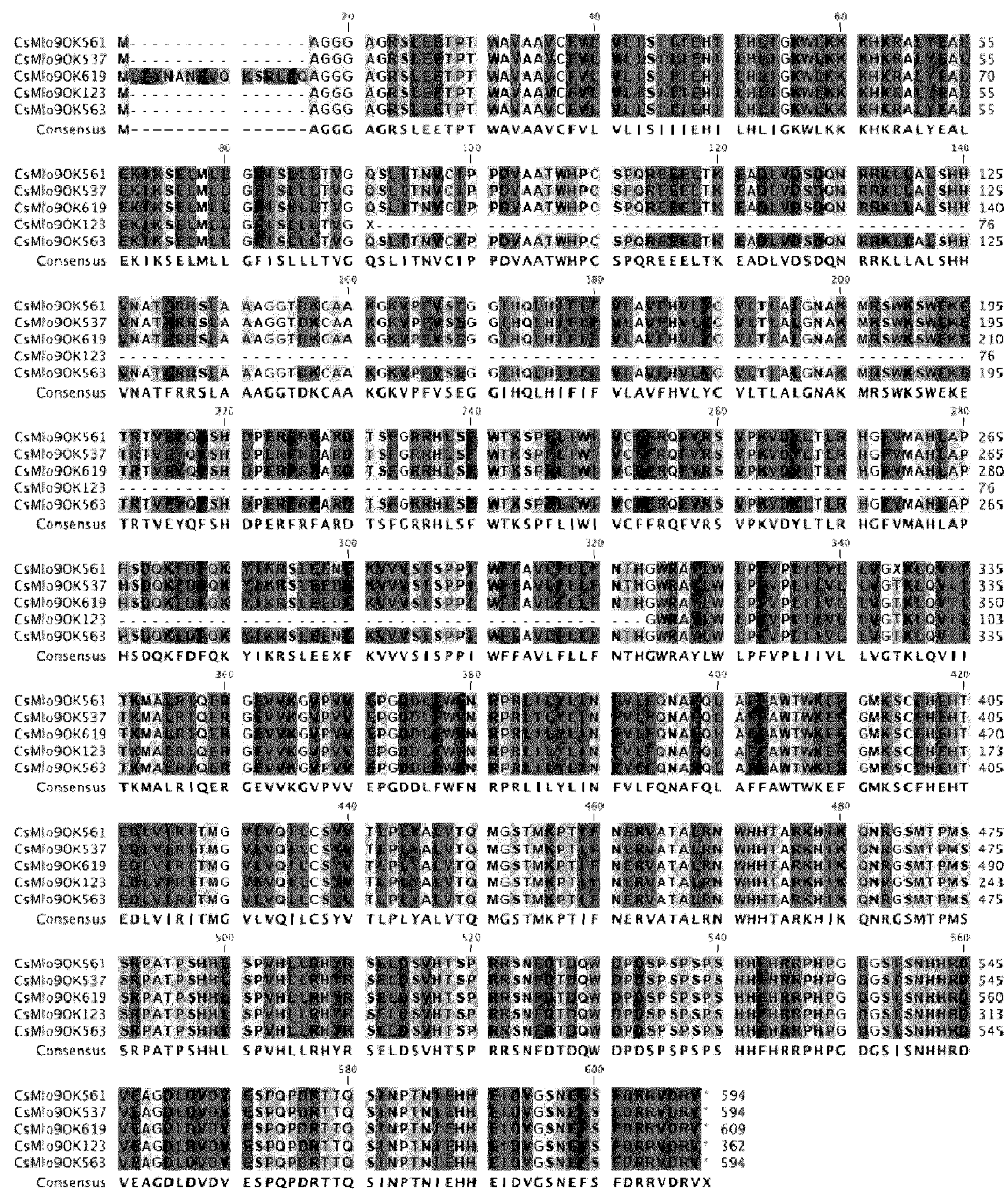
FIG. 4: shows an amino acid alignment of CsKIP9 alleles of powdery mildew susceptible and powdery mildew resistant CsKIP9 alleles. The amino acid sequences shown in FIG. 4 correspond with the following SEQ ID Nos.

The amino acid sequences encoded by the cDNAs were aligned as shown in FIG. 4. An amino acid substitution of asparagine (N) by aspartic acid (D) (LEEN to LEED) at position 284 of CsKIP9 (SEQ ID No. 2) was found to correlate with the powdery mildew resistance observed.

Example 3

Powdery Mildew Resistant Cucumber Plant with Non-Function CsKIP9

The cDNA sequence CsKIP9 of a powdery mildew resistant cucumber plant was determined and an amino acid substation in exon 3 was defined. Specifically, the coding sequence of the first amino acids of exon 3 (positions 61 to 63 of SEQ ID No. 2) of functional CsKIP9 are Glutamic acid (E)-Leucine (L)-Methionine (M) [ELM]. However, in the powdery mildew resistant cucumber plant identified, this sequence was mutated to Alanine (A)-Threonine (T)-Isoleucine (I) [ATI] indicating that this substitution in CsKIP9 correlates with the powdery mildew resistance observed.

The powdery mildew resistance providing genes identified herein are summarized in table 3 below. The cDNA and amino acid sequences provided are the powdery mildew resistant genes in their functional form, i.e. providing powdery mildew resistance when impaired at the protein level, such as by mutation, or impaired at the expression level.

TABLE 3 cDNA and amino acid sequences of the present genes

| gene identity | Plant | Sequence type | SEQ ID No. |
|---|---|---|---|
| CsKIP9 | *Cucumis sativus* | cDNA | 1 |
| | | Aa | 2 |
| CsKIP2 | *Cucumis sativus* | cDNA | 3 |
| | | aa | 4 |
| CsKIP1 | *Cucumis sativus* | cDNA | 5 |
| | | aa | 6 |
| CsKIP3 | *Cucumis sativus* | cDNA | 7 |
| | | aa | 8 |
| CsKIP4 | *Cucumis sativus* | cDNA | 9 |
| | | aa | 10 |
| CsKIP5 | *Cucumis sativus* | cDNA | 11 |
| | | aa | 12 |
| CsKIP6 | *Cucumis sativus* | cDNA | 13 |
| | | aa | 14 |
| CsKIP7 | *Cucumis sativus* | cDNA | 15 |
| | | aa | 16 |
| CsKIP8 | *Cucumis sativus* | cDNA | 17 |
| | | aa | 18 |
| CsKIP10 | *Cucumis sativus* | cDNA | 19 |
| | | aa | 20 |
| CsKIP11 | *Cucumis sativus* | cDNA | 21 |
| | | aa | 22 |

The invention claimed is:

1. An isolated cucumber plant that is resistant to powdery mildew comprising in its genome an impaired powdery-mildew susceptibility gene, wherein the presence of the impaired powdery-mildew susceptibility gene is determinable by an absence or loss of function SEQ ID NO: 2 compared to a cucumber plant that is susceptible to powdery mildew, wherein the impairment is one or more non-natural mutations that cause an absence or loss of function SEQ ID NO: 2.

2. A seed, fruit, plant part, or propagation material of the cucumber plant according to claim 1, wherein the seed, fruit, plant part, or propagation material comprises the one or more non-natural mutations that causes an absence or loss of function of SEQ ID NO: 2, and wherein the seed, fruit, plant part, or propagation material exhibits resistance to powdery mildew.

3. A method for obtaining a cucumber plant that is resistant to powdery mildew, comprising introducing an impairment comprising one or more non-natural mutations to a nucleotide sequence having a sequence of SEQ ID NO: 1 in a cucumber plant that is susceptible to powdery mildew, wherein the impairment causes an absence or loss of function of SEQ ID NO: 2.

4. The method according to claim 3, wherein the one or more non-natural mutations cause the absence of SEQ ID NO: 2.

5. The method according to claim 3, wherein the one or more non-natural mutations cause a non-functioning SEQ ID NO: 2.

6. The isolated cucumber plant according to claim 1, wherein the impairment causes a substitution of at least one amino acid at positions 61-63 of SEQ ID NO: 2.

7. The isolated cucumber plant according to claim 6, wherein the substitution of at least one amino acid at positions 61-63 of SEQ ID NO: 2 is a substitution that results in replacement of glutamic acid-leucine-methionine with alanine-threonine-isoleucine.

8. The isolated cucumber plant according to claim 1, wherein the impairment causes lengthening of an N-terminal region of SEQ ID NO: 2, wherein the lengthening comprises amino acids 2-16 of SEQ ID NO: 31 (LFYNANFVQKSR-LFQ).

9. The isolated cucumber plant according to claim 1, wherein the impairment causes an amino acid substitution at position 284 of SEQ ID NO: 2.

10. The isolated cucumber plant according to claim 9, wherein the amino acid substitution at position 284 of SEQ ID NO: 2 is a substitution of asparagine for aspartic acid.

11. The isolated cucumber plant according to claim 1, wherein the impairment is a deletion in a coding region of a nucleic acid sequence having the sequence SEQ ID NO: 1.

12. The isolated cucumber plant according to claim 11, wherein the deletion is in exon 11.

13. The isolated cucumber plant according to claim 11, wherein the deletion is of at least 72 base pairs.

14. A plant produced by the method according to claim 3, wherein the plant comprises the one or more non-natural mutations of SEQ ID NO: 1, and wherein the plant exhibits resistance to powdery mildew.

15. A seed, fruit, plant part, or propagation material of the cucumber plant produced according to the method of claim 3, wherein the seed, fruit, plant part, or propagation material comprises the one or more non-natural mutations of SEQ ID NO: 1, and wherein the seed, fruit, plant part, or propagation material exhibits resistance to powdery mildew.

* * * * *

UNITED STATES PATENT AND TRADEMARK OFFICE

CERTIFICATE OF CORRECTION

PATENT NO. : 9,493,787 B2
APPLICATION NO. : 14/002284
DATED : November 15, 2016
INVENTOR(S) : Paul Johan Diergaarde et al.

It is certified that error appears in the above-identified patent and that said Letters Patent is hereby corrected as shown below:

In the Claims

Column 77, Line 49, Claim 1, after “function” insert -- of --

Signed and Sealed this
Seventh Day of March, 2017

Michelle K. Lee
*Director of the United States Patent and Trademark Office*

SEQUENCE LISTING

```
<160> NUMBER OF SEQ ID NOS: 34

<210> SEQ ID NO 1
<211> LENGTH: 1782
<212> TYPE: DNA
<213> ORGANISM: Cucumis sativus

<400> SEQUENCE: 1

atggccggag gtggcgccgg aaggtccttg gaagagacgc cgacatgggc cgtcgccgcc      60
```

```
gtgtgctttg ttttggttct gatttctatt atcatcgaac acattctcca tctcatcgga    120

aagtggctaa agaagaaaca caaacgagct ctctacgaag ctctggagaa gattaaatca    180

gaactgatgc tgttgggatt catatcgctg ctgctgacgg tgggacaaag cctaatcaca    240

aatgtttgta taccacctga cgtggcagcc acgtggcatc catgtagtcc tcaaagagaa    300

gaagaattaa ctaaagaagc tgacctcgtc gattccgacc aaaatcgtcg aaaacttctc    360

gccctctccc atcacgtcaa cgccaccttc cgccgttccc tcgccgctgc cggtggtacc    420

gacaaatgtg ctgccaaggg taaagttcca tttgtatcgg aagggggtat tcatcagcta    480

catatattca tcttcgtact ggcagttttc catgttttgt attgtgtttt aactttagct    540

ttgggcaatg ccaagatgag aagttggaag tcatgggaaa aagagacaag aactgtggag    600

tatcaattct cacacgatcc ggaacggttt cgatttgcaa gagacacgtc atttgggaga    660

agacacttaa gcttttggac aaaatcccct ttcctcatat ggattgtttg tttcttcaga    720

caattcgtta ggtcggttcc aaaggttgat tacttgacct taagacatgg tttcgtcatg    780

gcacatctgg caccgcacag cgatcagaaa tttgactttc aaaaatacat aaaacgatct    840

cttgaagaaa atttcaaggt ggtggtcagt atcagccctc cgatatggtt ctttgctgtc    900

ctcttcctac ttttcaacac ccacgggtgg agggcttatc tatggctacc ctttgttccg    960

ttaattatag tgttattggt ggggacaaag ttgcaagtga taataacgaa aatggcgctg   1020

aggatacaag aaagaggaga agtggtgaaa ggagtgccgg tggtagagcc aggggatgac   1080

ctttttttggt tcaatcgccc tcgtcttatt ctttacctta tcaattttgt cctcttccag   1140

aatgcctttc agcttgcctt ttttgcttgg acttggaaag aatttgggat gaaatcttgt   1200

ttccatgagc acacagagga tttggtcatc agaataacaa tgggggttct cgttcaaatc   1260

ctttgcagtt atgtcacact gccactttac gctctagtca cacagatggg ttcgacgatg   1320

aagcccacga ttttcaacga aagagtagcg acggcgttga gaaactggca ccacactgct   1380

cgtaaacaca taaaacaaaa tcgtggctca atgacgccga tgtcgagccg ccctgcaacc   1440

ccctcccacc acttgtcacc cgtccacctc cttcgccact atcgaagcga attagatagc   1500

gttcatacgt ctcctagaag atccaatttc gacaccgatc agtgggaccc tgattcccct   1560

tccccttccc cttcccacca ctttcaccgc cgtccccatc ccggcgacgg ctccatttcc   1620

aaccatcacc gtgatgtgga ggccggggat cttgatgtcg atgttgaatc gcctcaaccc   1680

gaccgaacga cccagtcaat aaacccaaca aatattgagc accatgaaat tgacgtgggg   1740

tctaacgaat tctcattcga tagaagagtt gatagagtat aa                      1782
```

<210> SEQ ID NO 2
<211> LENGTH: 593
<212> TYPE: PRT
<213> ORGANISM: Cucumis sativus

<400> SEQUENCE: 2

```
Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gln Ser Leu Ile Thr
```

```
65                  70                  75                  80

Asn Val Cys Ile Pro Pro Asp Val Ala Ala Thr Trp His Pro Cys Ser
                85                  90                  95

Pro Gln Arg Glu Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160

His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asn Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495
```

```
Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
            580                 585                 590

Val


<210> SEQ ID NO 3
<211> LENGTH: 1725
<212> TYPE: DNA
<213> ORGANISM: Cucumis sativus

<400> SEQUENCE: 3

atggctgaat gtggaacaga gcagcgtact ttggaagata cctcaacttg ggctgttgcg     60

gttgtttgtt ttttcttggt tgttatttca atcttcattg aacatgtcat tcacctcact    120

ggaaagtggc tggagaaaag gcacaagcca gctcttgttg aagctctaga aaaggttaaa    180

gcagagctta tgctattggg attcatatcc ctacttctaa cgataggcca agatgctgtc    240

actcaaattt gtgtttcgaa agagcttgca gcaacttggc ttccctgtgc agcaagagct    300

aaaacaggag taaaagttgc gaagaacagt cgtcttagac ttcttgaatt tttagatcct    360

gactatggtt cgaggcgtat tttagcctcg aaaggagatg atgcatgcgc taagaggggc    420

caactcgctt tcgtgtcggc atatggaatc catcagctcc atattttcat cttcgtattg    480

gctgtcttcc atgtcctgta ctgcatcata actttggctt ttggcagaac aaagatgagc    540

aaatggaagg cctgggagga tgaaaccaag acaattgaat accagtacta taatgatcca    600

gcaagattta gatttgctag agatactacg tttggacgcc gacacttgag cttctggagt    660

cgtacaccaa tttccctctg gattgtttgt ttcttcagac agttctttgg atcagttacc    720

aaggttgatt acatgacact gagacatgga ttcattgttg cacatcttgc acccggaagt    780

gaagtaaaat ttgatttcca caaatacatt agcagatctc tggaagacga ctttaaagtt    840

gttgtgggga ttagtcccgc aatgtggcta tttgctgttc tcttcatcct aaccaataca    900

aatgggtggt attcatatct atggctgcct ttcatctcct taattataat tctattggtg    960

ggaacaaagc tccatgttat tataactcat atgggattga caattcaaga aaggggtcat   1020

gttgtgaagg gtgttcccgt cgttcagcct cgggatgacc tgttttggtt tggacgtcca   1080

caacttattc tcttcctgat ccactttgtt ctctttatga atgcatttca gcttgccttc   1140

tttgcttgga ccacatatgc atttaagtgg atgggttgtt tccatcagcg agttgaagat   1200

attgtcatca gactctcaat gggggttatc atacaagttc tctgcagtta tgtcacactc   1260

ccactctatg ctttggttac tcagatgggc tctaacatga gaccaaccat tttcaacgac   1320

cgagtggcga cggcattgaa gaactggcac cactcagcca agaagaacat gaagcagcac   1380

cgcaacccag acagtacctc accattctca agcaggccag ctactccaac tcacggcatg   1440

tctcctattc accttctgca caaacatcag catggcagca catctcccag gctatccgat   1500
```

-continued

```
gccgaacccg atcgttggga agagttgcct ccttcttcac accatagtag agccccccat   1560

catgataatc atcaagatca acaagaacaa tctgagacaa taattagaga acaggagatg   1620

acagttcaag gaccaagttc aagtgaaacc ggttccataa cacgtcctgc tcgccctcat   1680

caggaaatca ctaggactcc atcagacttc tcatttgcca aatga                   1725


<210> SEQ ID NO 4
<211> LENGTH: 574
<212> TYPE: PRT
<213> ORGANISM: Cucumis sativus

<400> SEQUENCE: 4

Met Ala Glu Cys Gly Thr Glu Gln Arg Thr Leu Glu Asp Thr Ser Thr
1               5                   10                  15

Trp Ala Val Ala Val Val Cys Phe Phe Leu Val Val Ile Ser Ile Phe
            20                  25                  30

Ile Glu His Val Ile His Leu Thr Gly Lys Trp Leu Glu Lys Arg His
        35                  40                  45

Lys Pro Ala Leu Val Glu Ala Leu Glu Lys Val Lys Ala Glu Leu Met
    50                  55                  60

Leu Leu Gly Phe Ile Ser Leu Leu Leu Thr Ile Gly Gln Asp Ala Val
65                  70                  75                  80

Thr Gln Ile Cys Val Ser Lys Glu Leu Ala Ala Thr Trp Leu Pro Cys
                85                  90                  95

Ala Ala Arg Ala Lys Thr Gly Val Lys Val Ala Lys Asn Ser Arg Leu
            100                 105                 110

Arg Leu Leu Glu Phe Leu Asp Pro Asp Tyr Gly Ser Arg Arg Ile Leu
        115                 120                 125

Ala Ser Lys Gly Asp Asp Ala Cys Ala Lys Arg Gly Gln Leu Ala Phe
    130                 135                 140

Val Ser Ala Tyr Gly Ile His Gln Leu His Ile Phe Ile Phe Val Leu
145                 150                 155                 160

Ala Val Phe His Val Leu Tyr Cys Ile Ile Thr Leu Ala Phe Gly Arg
                165                 170                 175

Thr Lys Met Ser Lys Trp Lys Ala Trp Glu Asp Glu Thr Lys Thr Ile
            180                 185                 190

Glu Tyr Gln Tyr Tyr Asn Asp Pro Ala Arg Phe Arg Phe Ala Arg Asp
        195                 200                 205

Thr Thr Phe Gly Arg Arg His Leu Ser Phe Trp Ser Arg Thr Pro Ile
    210                 215                 220

Ser Leu Trp Ile Val Cys Phe Phe Arg Gln Phe Phe Gly Ser Val Thr
225                 230                 235                 240

Lys Val Asp Tyr Met Thr Leu Arg His Gly Phe Ile Val Ala His Leu
                245                 250                 255

Ala Pro Gly Ser Glu Val Lys Phe Asp Phe His Lys Tyr Ile Ser Arg
            260                 265                 270

Ser Leu Glu Asp Asp Phe Lys Val Val Val Gly Ile Ser Pro Ala Met
        275                 280                 285

Trp Leu Phe Ala Val Leu Phe Ile Leu Thr Asn Thr Asn Gly Trp Tyr
    290                 295                 300

Ser Tyr Leu Trp Leu Pro Phe Ile Ser Leu Ile Ile Ile Leu Leu Val
305                 310                 315                 320

Gly Thr Lys Leu His Val Ile Ile Thr His Met Gly Leu Thr Ile Gln
                325                 330                 335
```

```
Glu Arg Gly His Val Val Lys Gly Val Pro Val Val Gln Pro Arg Asp
            340                 345                 350

Asp Leu Phe Trp Phe Gly Arg Pro Gln Leu Ile Leu Phe Leu Ile His
        355                 360                 365

Phe Val Leu Phe Met Asn Ala Phe Gln Leu Ala Phe Phe Ala Trp Thr
    370                 375                 380

Thr Tyr Ala Phe Lys Trp Met Gly Cys Phe His Gln Arg Val Glu Asp
385                 390                 395                 400

Ile Val Ile Arg Leu Ser Met Gly Val Ile Ile Gln Val Leu Cys Ser
                405                 410                 415

Tyr Val Thr Leu Pro Leu Tyr Ala Leu Val Thr Gln Met Gly Ser Asn
            420                 425                 430

Met Arg Pro Thr Ile Phe Asn Asp Arg Val Ala Thr Ala Leu Lys Asn
        435                 440                 445

Trp His His Ser Ala Lys Lys Asn Met Lys Gln His Arg Asn Pro Asp
    450                 455                 460

Ser Thr Ser Pro Phe Ser Ser Arg Pro Ala Thr Pro Thr His Gly Met
465                 470                 475                 480

Ser Pro Ile His Leu Leu His Lys His Gln His Gly Ser Thr Ser Pro
                485                 490                 495

Arg Leu Ser Asp Ala Glu Pro Asp Arg Trp Glu Glu Leu Pro Pro Ser
            500                 505                 510

Ser His His Ser Arg Ala Pro His His Asp Asn His Gln Asp Gln Gln
        515                 520                 525

Glu Gln Ser Glu Thr Ile Ile Arg Glu Gln Glu Met Thr Val Gln Gly
    530                 535                 540

Pro Ser Ser Ser Glu Thr Gly Ser Ile Thr Arg Pro Ala Arg Pro His
545                 550                 555                 560

Gln Glu Ile Thr Arg Thr Pro Ser Asp Phe Ser Phe Ala Lys
                565                 570


<210> SEQ ID NO 5
<211> LENGTH: 1749
<212> TYPE: DNA
<213> ORGANISM: Cucumis sativus

<400> SEQUENCE: 5

atggcggggg cagccggtgg caagtcgctg gagcaaacac cgacatgggc cgttgccgtt      60

gtttgctttg ttttgctcgt catctctatt ttcatcgaat atagtctcca tcttatcgga     120

cattggctaa agaagagaca caaacgggcg ttgtttgaag cattagagaa gatcaaatca     180

gagcttatgt tattggggtt tatatcattg ctactaacgg tggggcaagg accaataacg     240

gagatatgta ttccacaaca tgtagctgca acgtggcatc catgtacaaa ggaaagagaa     300

gatgagatga acaaagaggt ggagaaatct gtggaacatt tgggtcttga tcgccggaga     360

ctccttcatc tcctcggaaa tggtgaaagt ttccggcgga gtttggccgc tgcgggagga     420

gaggataaat gtgccgccaa gggtaaagct tcctttattt cagcagatgg aattcatcaa     480

cttcatatct tcatttttgt gttggcagtt tttcatgttt tgtattgtgt tctaacttat     540

gcgttggcta gagctaagat gaggagttgg aaaacatggg aaaaagagac caaaactgct     600

gaataccaat tctcacatga tccagagagg tttaggtttg caagagacac ctcatttggg     660

agaagacatt tgagcttttg gaccaaaaat cctgccttga tgtggatcgt tcgtttcttc     720

agacaatttg taagatctgt tccaaaagtt gattacttga cattaagaca tgggtttata     780
```

-continued

```
atggcacatt tagcacctca aagtcttaca caatttgatt ttcaaaaata cattaataga    840

tcccttgaag aagacttcaa agttgttgtg ggaatcagcc cgccaatttg gttctttgct    900

gttctatctc tcctctcaaa cactcacggt tggagggcgt atctatggct gccattcatc    960

ccactaatca ttttgctgtt gattggaaca aaattgcaag tgatcataac gaaaatggca   1020

ctaagaatac aagaaagagg tgaagtagtg aagggcgtgc cggtggtgga gcctggcggt   1080

gacctctttt ggtttaatcg gcctcgcctt attctttatc tcatcaactt tgttctcttt   1140

caaaatgcct tccaagttgc cttctttgct tggacttggt atgagtttgg gttgaattct   1200

tgcttccatg agcatataga agatgtggtg atcagaattt ctatgggggt gcttgtacaa   1260

atcctttgca gttatgttac tcttcctctt tatgcactag tcactcagat gggttcaaca   1320

atgaagccaa ctatattcaa tgagagagtg gcagaggccc ttcgcaattg gtaccactcg   1380

gctcgaaagc acatcaaaca caaccgcggt tcggtcactc caatgtcgag ccgacccgcc   1440

accccgactc acagcatgtc gcctgtccac cttctccgac actacaagag tgaagtcgat   1500

agcttccaca cctcaccgag aaggtcaccg ttcgacaccg atcgttggga caacgattcg   1560

ccctctccat ctcgccatgt tgatggttcg tcttcgtcac aaccccacgt tgagatggga   1620

ggttatgaaa aagatcccgt tgaatcaagt tcgtctcgag ttgatccggt tcaaccatct   1680

cgaaaccgca atcaacatga gattcatatt ggaggcccca aagacttttc atttgataga   1740

gttgaatga                                                           1749
```

<210> SEQ ID NO 6
<211> LENGTH: 582
<212> TYPE: PRT
<213> ORGANISM: Cucumis sativus

<400> SEQUENCE: 6

```
Met Ala Gly Ala Ala Gly Gly Lys Ser Leu Glu Gln Thr Pro Thr Trp
1               5                   10                  15

Ala Val Ala Val Val Cys Phe Val Leu Leu Val Ile Ser Ile Phe Ile
            20                  25                  30

Glu Tyr Ser Leu His Leu Ile Gly His Trp Leu Lys Lys Arg His Lys
        35                  40                  45

Arg Ala Leu Phe Glu Ala Leu Glu Lys Ile Lys Ser Glu Leu Met Leu
    50                  55                  60

Leu Gly Phe Ile Ser Leu Leu Leu Thr Val Gly Gln Gly Pro Ile Thr
65                  70                  75                  80

Glu Ile Cys Ile Pro Gln His Val Ala Ala Thr Trp His Pro Cys Thr
                85                  90                  95

Lys Glu Arg Glu Asp Glu Met Asn Lys Glu Val Glu Lys Ser Val Glu
            100                 105                 110

His Leu Gly Leu Asp Arg Arg Arg Leu Leu His Leu Leu Gly Asn Gly
        115                 120                 125

Glu Ser Phe Arg Arg Ser Leu Ala Ala Ala Gly Gly Glu Asp Lys Cys
    130                 135                 140

Ala Ala Lys Gly Lys Ala Ser Phe Ile Ser Ala Asp Gly Ile His Gln
145                 150                 155                 160

Leu His Ile Phe Ile Phe Val Leu Ala Val Phe His Val Leu Tyr Cys
                165                 170                 175

Val Leu Thr Tyr Ala Leu Ala Arg Ala Lys Met Arg Ser Trp Lys Thr
            180                 185                 190

Trp Glu Lys Glu Thr Lys Thr Ala Glu Tyr Gln Phe Ser His Asp Pro
```

```
        195                 200                 205

Glu Arg Phe Arg Phe Ala Arg Asp Thr Ser Phe Gly Arg Arg His Leu
    210                 215                 220

Ser Phe Trp Thr Lys Asn Pro Ala Leu Met Trp Ile Val Arg Phe Phe
225                 230                 235                 240

Arg Gln Phe Val Arg Ser Val Pro Lys Val Asp Tyr Leu Thr Leu Arg
                245                 250                 255

His Gly Phe Ile Met Ala His Leu Ala Pro Gln Ser Leu Thr Gln Phe
            260                 265                 270

Asp Phe Gln Lys Tyr Ile Asn Arg Ser Leu Glu Glu Asp Phe Lys Val
        275                 280                 285

Val Val Gly Ile Ser Pro Pro Ile Trp Phe Phe Ala Val Leu Ser Leu
    290                 295                 300

Leu Ser Asn Thr His Gly Trp Arg Ala Tyr Leu Trp Leu Pro Phe Ile
305                 310                 315                 320

Pro Leu Ile Ile Leu Leu Leu Ile Gly Thr Lys Leu Gln Val Ile Ile
                325                 330                 335

Thr Lys Met Ala Leu Arg Ile Gln Glu Arg Gly Glu Val Val Lys Gly
            340                 345                 350

Val Pro Val Val Glu Pro Gly Gly Asp Leu Phe Trp Phe Asn Arg Pro
        355                 360                 365

Arg Leu Ile Leu Tyr Leu Ile Asn Phe Val Leu Phe Gln Asn Ala Phe
    370                 375                 380

Gln Val Ala Phe Phe Ala Trp Thr Trp Tyr Glu Phe Gly Leu Asn Ser
385                 390                 395                 400

Cys Phe His Glu His Ile Glu Asp Val Val Ile Arg Ile Ser Met Gly
                405                 410                 415

Val Leu Val Gln Ile Leu Cys Ser Tyr Val Thr Leu Pro Leu Tyr Ala
            420                 425                 430

Leu Val Thr Gln Met Gly Ser Thr Met Lys Pro Thr Ile Phe Asn Glu
        435                 440                 445

Arg Val Ala Glu Ala Leu Arg Asn Trp Tyr His Ser Ala Arg Lys His
    450                 455                 460

Ile Lys His Asn Arg Gly Ser Val Thr Pro Met Ser Ser Arg Pro Ala
465                 470                 475                 480

Thr Pro Thr His Ser Met Ser Pro Val His Leu Leu Arg His Tyr Lys
                485                 490                 495

Ser Glu Val Asp Ser Phe His Thr Ser Pro Arg Arg Ser Pro Phe Asp
            500                 505                 510

Thr Asp Arg Trp Asp Asn Asp Ser Pro Ser Pro Ser Arg His Val Asp
        515                 520                 525

Gly Ser Ser Ser Ser Gln Pro His Val Glu Met Gly Gly Tyr Glu Lys
    530                 535                 540

Asp Pro Val Glu Ser Ser Ser Ser Arg Val Asp Pro Val Gln Pro Ser
545                 550                 555                 560

Arg Asn Arg Asn Gln His Glu Ile His Ile Gly Gly Pro Lys Asp Phe
                565                 570                 575

Ser Phe Asp Arg Val Glu
            580
```

```
<210> SEQ ID NO 7
<211> LENGTH: 1551
<212> TYPE: DNA
<213> ORGANISM: Cucumis sativus
```

<400> SEQUENCE: 7

```
atgggtggcg gaggtgaagg aacgacgctg gaattcactc cgacgtgggt tgtagccgcc     60
gtatgtactg tcatcgttgc catttctctc gccttagagc gccttcttca ctttctcggc    120
agatacctca aaagcaagaa tcaaaagccg ctcaatgaag ctcttcagaa agttaaagaa    180
gaattgatgc ttttggggtt catttcactt ctgctcactg tatttcaagg caccatctct    240
aaattgtgtg ttcctgagag tttgactgaa catttacttc cgtgtgatct gaaggataaa    300
ccgaaagctg aacatggttc gccctctggt gaatctggtt cgtcaacgac gaagcatttt    360
caaacgttat ttgtttcgag tatttctggt acggccaggc ggcttctttc tgagggatct    420
gcttcacaag ctggttactg tgccaaaaag aataaggtgc cattgctatc tcttgaagca    480
ttgcatcatc tacatatttt tatcttcatc ctagctatcg tccacgtgac attttgcgtt    540
ctcactgtag tttttggagg attgaagatt cgccagcgga agcattggga ggattctatt    600
gcaaaagaga attatgatac tgaacaagtt ctaaaaccaa aggtcactca tgtccatcaa    660
catgttttta tcaaagacca ctttttgggc tttggtaaag attcagctct tcttggttgg    720
ttgcattcat ttctcaagca attttatgct tctgtaacaa aatcagatta tgcaacgtta    780
cgacttggtt tcattacgac gcactgcagg ggaaatccaa agtttaattt tcacaagtac    840
atgatacgtg cccttgaaga tgacttcaag catgttgttg gtatcagttg gtatctttgg    900
atattcgtgg ttgtcttctt gttccttaat gtcagtggtt ggcatacata tttctggata    960
gcattcattc ctttcgttct tctgcttgct gtgggaacga agctggaaca tgtgataacc   1020
cagctggctc atgaggttgc agagaagcac atagcaatcg aaggtgatct agtagtccaa   1080
ccgtctgatg atcacttttg gttccaacgt ccccgtattg ttctcttctt gatccacttt   1140
atacttttcc aaaacgcttt tgagattgga tttttcttct ggatatgggt tcaatatgga   1200
tttgactcgt gcatcatggg acaagtccgc tatatcattc caaggctcat cattggggtg   1260
tttgttcagg ttctttgcag ttacagcacc cttctgctct gcgccattgt cactcagatg   1320
ggaagttctt tcaagaaagc aatctttgat gaacatgtac aagtagggct agttggctgg   1380
gctcagaagg tgaagaaaag aaagggactt agagcagctg ctgatggctc cagtcaagga   1440
gtcaaggaag gtggttcaac tgtggggatt cagttgggaa atgttatgcg caaggcttct   1500
gcacctcaag aaattaagcc tgatgactcc aaatcaaatg atattcctta g            1551
```

<210> SEQ ID NO 8
<211> LENGTH: 516
<212> TYPE: PRT
<213> ORGANISM: Cucumis sativus

<400> SEQUENCE: 8

```
Met Gly Gly Gly Gly Glu Gly Thr Thr Leu Glu Phe Thr Pro Thr Trp
1               5                   10                  15

Val Val Ala Ala Val Cys Thr Val Ile Val Ala Ile Ser Leu Ala Leu
            20                  25                  30

Glu Arg Leu Leu His Phe Leu Gly Arg Tyr Leu Lys Ser Lys Asn Gln
        35                  40                  45

Lys Pro Leu Asn Glu Ala Leu Gln Lys Val Lys Glu Glu Leu Met Leu
    50                  55                  60

Leu Gly Phe Ile Ser Leu Leu Leu Thr Val Phe Gln Gly Thr Ile Ser
65                  70                  75                  80

Lys Leu Cys Val Pro Glu Ser Leu Thr Glu His Leu Leu Pro Cys Asp
```

```
                85                  90                  95

Leu Lys Asp Lys Pro Lys Ala Glu His Gly Ser Pro Ser Gly Glu Ser
            100                 105                 110

Gly Ser Ser Thr Thr Lys His Phe Gln Thr Leu Phe Val Ser Ser Ile
        115                 120                 125

Ser Gly Thr Ala Arg Arg Leu Leu Ser Glu Gly Ser Ala Ser Gln Ala
    130                 135                 140

Gly Tyr Cys Ala Lys Lys Asn Lys Val Pro Leu Leu Ser Leu Glu Ala
145                 150                 155                 160

Leu His His Leu His Ile Phe Ile Phe Ile Leu Ala Ile Val His Val
                165                 170                 175

Thr Phe Cys Val Leu Thr Val Val Phe Gly Gly Leu Lys Ile Arg Gln
            180                 185                 190

Arg Lys His Trp Glu Asp Ser Ile Ala Lys Glu Asn Tyr Asp Thr Glu
        195                 200                 205

Gln Val Leu Lys Pro Lys Val Thr His Val His Gln His Val Phe Ile
    210                 215                 220

Lys Asp His Phe Leu Gly Phe Gly Lys Asp Ser Ala Leu Leu Gly Trp
225                 230                 235                 240

Leu His Ser Phe Leu Lys Gln Phe Tyr Ala Ser Val Thr Lys Ser Asp
                245                 250                 255

Tyr Ala Thr Leu Arg Leu Gly Phe Ile Thr Thr His Cys Arg Gly Asn
            260                 265                 270

Pro Lys Phe Asn Phe His Lys Tyr Met Ile Arg Ala Leu Glu Asp Asp
        275                 280                 285

Phe Lys His Val Val Gly Ile Ser Trp Tyr Leu Trp Ile Phe Val Val
    290                 295                 300

Val Phe Leu Phe Leu Asn Val Ser Gly Trp His Thr Tyr Phe Trp Ile
305                 310                 315                 320

Ala Phe Ile Pro Phe Val Leu Leu Leu Ala Val Gly Thr Lys Leu Glu
                325                 330                 335

His Val Ile Thr Gln Leu Ala His Glu Val Ala Glu Lys His Ile Ala
            340                 345                 350

Ile Glu Gly Asp Leu Val Val Gln Pro Ser Asp Asp His Phe Trp Phe
        355                 360                 365

Gln Arg Pro Arg Ile Val Leu Phe Leu Ile His Phe Ile Leu Phe Gln
    370                 375                 380

Asn Ala Phe Glu Ile Gly Phe Phe Phe Trp Ile Trp Val Gln Tyr Gly
385                 390                 395                 400

Phe Asp Ser Cys Ile Met Gly Gln Val Arg Tyr Ile Ile Pro Arg Leu
                405                 410                 415

Ile Ile Gly Val Phe Val Gln Val Leu Cys Ser Tyr Ser Thr Leu Leu
            420                 425                 430

Leu Cys Ala Ile Val Thr Gln Met Gly Ser Ser Phe Lys Lys Ala Ile
        435                 440                 445

Phe Asp Glu His Val Gln Val Gly Leu Val Gly Trp Ala Gln Lys Val
    450                 455                 460

Lys Lys Arg Lys Gly Leu Arg Ala Ala Ala Asp Gly Ser Ser Gln Gly
465                 470                 475                 480

Val Lys Glu Gly Gly Ser Thr Val Gly Ile Gln Leu Gly Asn Val Met
                485                 490                 495

Arg Lys Ala Ser Ala Pro Gln Glu Ile Lys Pro Asp Asp Ser Lys Ser
            500                 505                 510
```

Asn Asp Ile Pro
515

<210> SEQ ID NO 9
<211> LENGTH: 1641
<212> TYPE: DNA
<213> ORGANISM: Cucumis sativus

<400> SEQUENCE: 9
atgttgctgg ttgtttatta tttgtgcttg agcttgttgt gggggaaatc gtggggggct 60
ccggccagcg atggcaccac gagggagctc gatcagactc cgacatgggc tgttgctggt 120
gtttgtgcta ttattatcct tatttctatc gccttggaga aactccttca taaagctgga 180
acgtggctca cggaaaagca caagagagct ctctttgaag ctctggagaa agttaaagct 240
gagctgatga ttctgggttt catttcactg ctcctcacct ttggacagaa ctacatcatt 300
aaaatatgca ttcccacaaa ggttgcaaat actatgttgc catgtgctgc caaagaggac 360
aaattggaga agggagatga aggcgaacat catcgacgac ttctaatgta tgaacggagg 420
ttcctggctg ctgctggtgg cgctgttagt tgcaaagaag gtcatgtgcc gcttatatct 480
atctcgggat tgcatcagtt gcacttgttt atcttcttct tagccgtatt tcatgtggta 540
tatagtgcca tcacaatgat gcttgggagg ctaaagattc gaggttggaa ggcatgggag 600
gaggagacct caactcacaa ttatgagttc tcaaatgata atgcacgatt caggcttact 660
cacgaaacat catttgtgaa agcccacacg agtttttgga caaaacttcc cgtcttcttt 720
tatattggat gcttcttccg acaatttttc aagtccgttg gtcaccttgc tccgggaagt 780
aaatttgact ttcaaaaata tatcaaaagg tctctagaag atgacttcaa aataattgtg 840
ggagttagtc ccgtgctttg gacatcgttt gtggtcttct tgctcataaa tgtttacgga 900
tggcaagcat tgttttggtc atccttagtt cctgtgatca taatcctagc tgttggaacc 960
aagcttcaag gagttatgac aaagatggct ctcgaaatta cagaaagaca tgctgttgtc 1020
caaggaattc ctctcgttca ggcatcagat aaatattttt ggtttggcaa gcctcagctg 1080
gttctttacc tcatccactt cgctttattt tcgaatgcat tccaaataac atacttcttc 1140
tggatttggt attcctttgg gttaaaatcc tgcttccata ctgatttcaa gctcgcaatc 1200
attaaagttg gtctcggggt tggcgttctc tgtctctgca gttatataac tcttccactc 1260
tatgctcttg tcactcagat gggtacgcgt atgaagaagt caatctttga tgaacaaaca 1320
tcgaaggctc ttaagaagtg gcacatggct gttaagaagc gacatgggaa gtccccaact 1380
cgaaaactag ggagtccaag ttcatcacca attcatccat catcaggata cgcattgcat 1440
cgtttcaaga ccacaggtca ctcgaacaga tcatccatgt atgatgagaa tgacgcatca 1500
gattatgaag tcgacactcc aaattttaca gttagaatag accatggtga tgaacatcaa 1560
gctgaaataa ttgaacccca gcatacagaa aaaaggaatg aagacgattt ctcttttgtc 1620
aaacctggac carsgaaatg a 1641

<210> SEQ ID NO 10
<211> LENGTH: 546
<212> TYPE: PRT
<213> ORGANISM: Cucumis sativus

<400> SEQUENCE: 10

Met Leu Leu Val Val Tyr Tyr Leu Cys Leu Ser Leu Leu Trp Gly Lys
1 5 10 15

```
Ser Trp Gly Ala Pro Ala Ser Asp Gly Thr Thr Arg Glu Leu Asp Gln
            20                  25                  30

Thr Pro Thr Trp Ala Val Ala Gly Val Cys Ala Ile Ile Ile Leu Ile
        35                  40                  45

Ser Ile Ala Leu Glu Lys Leu Leu His Lys Ala Gly Thr Trp Leu Thr
    50                  55                  60

Glu Lys His Lys Arg Ala Leu Phe Glu Ala Leu Glu Lys Val Lys Ala
65                  70                  75                  80

Glu Leu Met Ile Leu Gly Phe Ile Ser Leu Leu Leu Thr Phe Gly Gln
                85                  90                  95

Asn Tyr Ile Ile Lys Ile Cys Ile Pro Thr Lys Val Ala Asn Thr Met
            100                 105                 110

Leu Pro Cys Ala Ala Lys Glu Asp Lys Leu Glu Lys Gly Asp Glu Gly
        115                 120                 125

Glu His His Arg Arg Leu Leu Met Tyr Glu Arg Arg Phe Leu Ala Ala
    130                 135                 140

Ala Gly Gly Ala Val Ser Cys Lys Glu Gly His Val Pro Leu Ile Ser
145                 150                 155                 160

Ile Ser Gly Leu His Gln Leu His Leu Phe Ile Phe Phe Leu Ala Val
                165                 170                 175

Phe His Val Val Tyr Ser Ala Ile Thr Met Met Leu Gly Arg Leu Lys
            180                 185                 190

Ile Arg Gly Trp Lys Ala Trp Glu Glu Glu Thr Ser Thr His Asn Tyr
        195                 200                 205

Glu Phe Ser Asn Asp Asn Ala Arg Phe Arg Leu Thr His Glu Thr Ser
    210                 215                 220

Phe Val Lys Ala His Thr Ser Phe Trp Thr Lys Leu Pro Val Phe Phe
225                 230                 235                 240

Tyr Ile Gly Cys Phe Phe Arg Gln Phe Phe Lys Ser Val Gly His Leu
                245                 250                 255

Ala Pro Gly Ser Lys Phe Asp Phe Gln Lys Tyr Ile Lys Arg Ser Leu
            260                 265                 270

Glu Asp Asp Phe Lys Ile Ile Val Gly Val Ser Pro Val Leu Trp Thr
        275                 280                 285

Ser Phe Val Val Phe Leu Leu Ile Asn Val Tyr Gly Trp Gln Ala Leu
    290                 295                 300

Phe Trp Ser Ser Leu Val Pro Val Ile Ile Ile Leu Ala Val Gly Thr
305                 310                 315                 320

Lys Leu Gln Gly Val Met Thr Lys Met Ala Leu Glu Ile Thr Glu Arg
                325                 330                 335

His Ala Val Val Gln Gly Ile Pro Leu Val Gln Ala Ser Asp Lys Tyr
            340                 345                 350

Phe Trp Phe Gly Lys Pro Gln Leu Val Leu Tyr Leu Ile His Phe Ala
        355                 360                 365

Leu Phe Ser Asn Ala Phe Gln Ile Thr Tyr Phe Phe Trp Ile Trp Tyr
    370                 375                 380

Ser Phe Gly Leu Lys Ser Cys Phe His Thr Asp Phe Lys Leu Ala Ile
385                 390                 395                 400

Ile Lys Val Gly Leu Gly Val Gly Val Leu Cys Leu Cys Ser Tyr Ile
                405                 410                 415

Thr Leu Pro Leu Tyr Ala Leu Val Thr Gln Met Gly Thr Arg Met Lys
            420                 425                 430

Lys Ser Ile Phe Asp Glu Gln Thr Ser Lys Ala Leu Lys Lys Trp His
```

```
        435                 440                 445

Met Ala Val Lys Lys Arg His Gly Lys Ser Pro Thr Arg Lys Leu Gly
    450                 455                 460

Ser Pro Ser Ser Ser Pro Ile His Pro Ser Ser Gly Tyr Ala Leu His
465                 470                 475                 480

Arg Phe Lys Thr Thr Gly His Ser Asn Arg Ser Ser Met Tyr Asp Glu
                485                 490                 495

Asn Asp Ala Ser Asp Tyr Glu Val Asp Thr Pro Asn Phe Thr Val Arg
            500                 505                 510

Ile Asp His Gly Asp Glu His Gln Ala Glu Ile Ile Glu Pro Gln His
        515                 520                 525

Thr Glu Lys Arg Asn Glu Asp Asp Phe Ser Phe Val Lys Pro Gly Pro
    530                 535                 540

Thr Lys
545


<210> SEQ ID NO 11
<211> LENGTH: 1638
<212> TYPE: DNA
<213> ORGANISM: Cucumis sativus

<400> SEQUENCE: 11

atgggtggcg gtgccggtgc cggtggtccg agtagggagt tagatcaaac tccgacatgg      60

gccgttgccg ctgtttgtgc agtcatcatt cttatttcca tcatattgga aaaggttctt     120

cacatggttg gagagatatt tcaaaaaagg aaaaagaaag ccttgtatga agcgctcgag     180

aaagttaaag gaggggagct tatggtttta ggattcattt ctttgctctt aacatttggg     240

caaaattata ttgctaaagt ttgtataccc tcaaagtatg aaaatactat gttgccttgc     300

ccttttagag ggagtagtac tactttacct aaaagctccc atcacgccga gcctgatgat     360

gatgaagaga cttccgatca ccatcgtagg cttctttggt acgagcatcg acgtctaggt     420

ggtggtggtt ctgtagaagg ttgcaaacca gggtatacac aacttatatc tctaaatggt     480

ttgcatcaaa tacatatctt catcttcttt ctagccgttc tccatgttgt atttagtgcc     540

ataacgatga ctctcggaag attgaaaatt cgtgcgtgga aggtatggga aagacagacc     600

gaacaagaac atgatgccat gaacgatcct acaaggttta gacttactca cgagacatcc     660

tttgtgagag atcacagcag tttttggacc aaaacccccc tctcctttta ctttgtatgc     720

ttctggaggc aattctttag gtccgttagt aggccagatt acttgtccct tagacatggt     780

tttgtcactg tccatttagc cctgggagt aaatttgact ttcagaagta cattaaaagg     840

tcattagaag atgactttaa ggtggtcgtg ggaatcagtc ctctgctatg ggcatcaatg     900

gtgctttttc tgcttctcaa tgttaatggg tggcaagtta tgttttgggt gtctatattt     960

cctctagtgg tgatcttagc tgttggaaca aagttgcaag gaattataac acaaatggct    1020

cttgaaatca aagaaagaca tgcagtggtt caagggattc cccttgttca agtctctgat    1080

agacattttt ggtttagttg gcccattttg gttctttatc tcatccatta tgtccttttc    1140

cagaatgcat ttgagattac atatttcttt tggatatggt atgaatttgg gttgagatca    1200

tgctttcatg acaactttga tcttattatc gcgagagttg gtctaggggt tggagtccag    1260

attttgtgca gttacattac actcccatta tatgctcttg taactcagat gggatcaaca    1320

atgaagaaat ccatatttga tgaacaaact tcgaaagcat tgaagcaatg gcatagaagt    1380

gctttgaaga aaaagaacga aggaggaaag cctgaaccaa cgccgatgcg aactttaggc    1440
```

-continued

```
ggtgccgttg ttgttggagg aagccctccc gagtcaccga tacaacaacc tttgcatgat   1500

caattccaac atcaaacaat gactcaatca tcaccaaccg acgtcgaagc ctccgccgtt   1560

ccttcagtca acataatgac taccgttgat ctccaccaac aacagcaaaa ctattccaat   1620

cgtgacttgt tgagatga                                                 1638


<210> SEQ ID NO 12
<211> LENGTH: 545
<212> TYPE: PRT
<213> ORGANISM: Cucumis sativus

<400> SEQUENCE: 12

Met Gly Gly Gly Ala Gly Ala Gly Gly Pro Ser Arg Glu Leu Asp Gln
1               5                   10                  15

Thr Pro Thr Trp Ala Val Ala Ala Val Cys Ala Val Ile Ile Leu Ile
            20                  25                  30

Ser Ile Ile Leu Glu Lys Val Leu His Met Val Gly Glu Ile Phe Gln
        35                  40                  45

Lys Arg Lys Lys Lys Ala Leu Tyr Glu Ala Leu Glu Lys Val Lys Gly
    50                  55                  60

Gly Glu Leu Met Val Leu Gly Phe Ile Ser Leu Leu Leu Thr Phe Gly
65                  70                  75                  80

Gln Asn Tyr Ile Ala Lys Val Cys Ile Pro Ser Lys Tyr Glu Asn Thr
                85                  90                  95

Met Leu Pro Cys Pro Phe Arg Gly Ser Ser Thr Thr Leu Pro Lys Ser
            100                 105                 110

Ser His His Ala Glu Pro Asp Asp Asp Glu Glu Thr Ser Asp His His
        115                 120                 125

Arg Arg Leu Leu Trp Tyr Glu His Arg Arg Leu Gly Gly Gly Gly Ser
    130                 135                 140

Val Glu Gly Cys Lys Pro Gly Tyr Thr Gln Leu Ile Ser Leu Asn Gly
145                 150                 155                 160

Leu His Gln Ile His Ile Phe Ile Phe Phe Leu Ala Val Leu His Val
                165                 170                 175

Val Phe Ser Ala Ile Thr Met Thr Leu Gly Arg Leu Lys Ile Arg Ala
            180                 185                 190

Trp Lys Val Trp Glu Arg Gln Thr Glu Gln Glu His Asp Ala Met Asn
        195                 200                 205

Asp Pro Thr Arg Phe Arg Leu Thr His Glu Thr Ser Phe Val Arg Asp
    210                 215                 220

His Ser Ser Phe Trp Thr Lys Thr Pro Leu Ser Phe Tyr Phe Val Cys
225                 230                 235                 240

Phe Trp Arg Gln Phe Phe Arg Ser Val Ser Arg Pro Asp Tyr Leu Ser
                245                 250                 255

Leu Arg His Gly Phe Val Thr Val His Leu Ala Pro Gly Ser Lys Phe
            260                 265                 270

Asp Phe Gln Lys Tyr Ile Lys Arg Ser Leu Glu Asp Asp Phe Lys Val
        275                 280                 285

Val Val Gly Ile Ser Pro Leu Leu Trp Ala Ser Met Val Leu Phe Leu
    290                 295                 300

Leu Leu Asn Val Asn Gly Trp Gln Val Met Phe Trp Val Ser Ile Phe
305                 310                 315                 320

Pro Leu Val Val Ile Leu Ala Val Gly Thr Lys Leu Gln Gly Ile Ile
                325                 330                 335
```

```
Thr Gln Met Ala Leu Glu Ile Lys Glu Arg His Ala Val Val Gln Gly
            340                 345                 350

Ile Pro Leu Val Gln Val Ser Asp Arg His Phe Trp Phe Ser Trp Pro
        355                 360                 365

Ile Leu Val Leu Tyr Leu Ile His Tyr Val Leu Phe Gln Asn Ala Phe
    370                 375                 380

Glu Ile Thr Tyr Phe Phe Trp Ile Trp Tyr Glu Phe Gly Leu Arg Ser
385                 390                 395                 400

Cys Phe His Asp Asn Phe Asp Leu Ile Ile Ala Arg Val Gly Leu Gly
                405                 410                 415

Val Gly Val Gln Ile Leu Cys Ser Tyr Ile Thr Leu Pro Leu Tyr Ala
            420                 425                 430

Leu Val Thr Gln Met Gly Ser Thr Met Lys Lys Ser Ile Phe Asp Glu
        435                 440                 445

Gln Thr Ser Lys Ala Leu Lys Gln Trp His Arg Ser Ala Leu Lys Lys
    450                 455                 460

Lys Asn Glu Gly Gly Lys Pro Glu Pro Thr Pro Met Arg Thr Leu Gly
465                 470                 475                 480

Gly Ala Val Val Val Gly Gly Ser Pro Pro Glu Ser Pro Ile Gln Gln
                485                 490                 495

Pro Leu His Asp Gln Phe Gln His Gln Thr Met Thr Gln Ser Ser Pro
            500                 505                 510

Thr Asp Val Glu Ala Ser Ala Val Pro Ser Val Asn Ile Met Thr Thr
        515                 520                 525

Val Asp Leu His Gln Gln Gln Gln Asn Tyr Ser Asn Arg Asp Leu Leu
    530                 535                 540

Arg
545
```

<210> SEQ ID NO 13
<211> LENGTH: 1872
<212> TYPE: DNA
<213> ORGANISM: Cucumis sativus

<400> SEQUENCE: 13

```
atggatggtg ggatccatcg tcccacccat tgggtcatcc aattcaataa tgttgaactt      60

catccctcat tttacacacc tttgattact acttcacttt actttttcca aaatttattc     120

cttttcttct tcttcttctt cttcttcttc ttcttctttc ttatgtctgt tttttgtctt     180

tgcttctgcc ttttattgac tggcgccgcc gcgtccggtg gagacggcgg ttcccactcc     240

agggatctcg ataacacacc cacctgggct gttgctgctg tttgcttctt tttcgttctt     300

atttccattg tcttggaaaa tgttattcac aaacttggaa cgtggttgac aaaaaagcac     360

aagagttctc tgtatgaagc tctggagaag gttaaggctg agttgatgat tttgggtttc     420

atctccctgc ttctgacttt tgctcaagca tatattgtcc aaatttgtat tcctccggcc     480

attgcaaact ccatgttgcc ccgtcgccgt gaagagaaaa atgcctcaac cgatgaagac     540

gaacatcacc ggagactaca atggctaatt cgaagatcat tggctggagg tcacaatgtt     600

gtctcgtgtg aggatggtaa ggtgtctctt atatccattg atggattgca tcagttgcat     660

attctcattt tcttcttagc tgtgtttcat gtgctcttta gtgttatcac aatgacactt     720

ggaaggataa agattcgagg ctggaaggag tgggagcagg aaacttcaac gcataactat     780

gagtttttca acgatcctgc aagatttagg cttactcacg agacatcttt tgtgaaagca     840

cacaccagct tttggacacg tcttcctttc ttcttctata ttagttgctt cttcaggcaa     900
```

-continued

```
ttttatgggt ctgttagtaa ggctgattac ttgacgctac gcaatggatt cataacagtt    960

catttagcac ctggaagtaa atttaacttc cagagatata tcaaaaggtc attagaagat   1020

gacttcaagg tagtcgtcgg tgtgagtcct tttctatggt cgtcatttgt gatcttcctg   1080

ctccttaatt tatctggatg gcatacattg ttctgggcat catttatccc tctgcttata   1140

atcttagccg ttggatcaaa acttcaagcc attttgacta gaatggctct tgaaatctct   1200

gagaaacatg cagtggtcca gggaattcca ctcgtgcaag gatccgacaa gtatttctgg   1260

ttcggccgcc ctcaactgat tcttcatctc atgcattttt ctttatttca gaatgcattc   1320

cagaccacct atattttgtc tacactgtat tcttttggcc tgaattcttg cttctttgat   1380

ggtcacatcc ttacaattat aaaagttggt ttaggggtag tagcattatt tctatgcagc   1440

tatgttacgc ttccaatata cgcccttgta aatcagatgg gttcaggtat gaagaggtcc   1500

atctttgatg aacagacatc aaaggcactc atgaaatggc aggaaacggc caagaagaag   1560

cgggctaaac gagcctcagc aactaaaacc ctcggaggta gttcaaatgc ttcacctcta   1620

cactcattgc gacggtttaa aactacagga cactccatac gtgtgcctac gtatgaggac   1680

cttgagtcat ctgattacga gggggatcca ttagcaacac ctacacaagc gtcaacaagt   1740

gaatcgatta atgttgatgt aaaagatgga gatgaaatac aacaaatcgc tgaaacagag   1800

caaccccaca gtacaattca aactaaagaa ggagatgagt tctcatttat aaagcctgca   1860

acactaggat aa                                                       1872


<210> SEQ ID NO 14
<211> LENGTH: 623
<212> TYPE: PRT
<213> ORGANISM: Cucumis sativus

<400> SEQUENCE: 14

Met Asp Gly Gly Ile His Arg Pro Thr His Trp Val Ile Gln Phe Asn
1               5                   10                  15

Asn Val Glu Leu His Pro Ser Phe Tyr Thr Pro Leu Ile Thr Thr Ser
            20                  25                  30

Leu Tyr Phe Phe Gln Asn Leu Phe Leu Phe Phe Phe Phe Phe Phe Phe
        35                  40                  45

Phe Phe Phe Phe Phe Leu Met Ser Val Phe Cys Leu Cys Phe Cys Leu
    50                  55                  60

Leu Leu Thr Gly Ala Ala Ala Ser Gly Gly Asp Gly Gly Ser His Ser
65                  70                  75                  80

Arg Asp Leu Asp Asn Thr Pro Thr Trp Ala Val Ala Ala Val Cys Phe
                85                  90                  95

Phe Phe Val Leu Ile Ser Ile Val Leu Glu Asn Val Ile His Lys Leu
            100                 105                 110

Gly Thr Trp Leu Thr Lys Lys His Lys Ser Ser Leu Tyr Glu Ala Leu
        115                 120                 125

Glu Lys Val Lys Ala Glu Leu Met Ile Leu Gly Phe Ile Ser Leu Leu
    130                 135                 140

Leu Thr Phe Ala Gln Ala Tyr Ile Val Gln Ile Cys Ile Pro Pro Ala
145                 150                 155                 160

Ile Ala Asn Ser Met Leu Pro Arg Arg Arg Glu Glu Lys Asn Ala Ser
                165                 170                 175

Thr Asp Glu Asp Glu His His Arg Arg Leu Gln Trp Leu Ile Arg Arg
            180                 185                 190
```

-continued

```
Ser Leu Ala Gly Gly His Asn Val Val Ser Cys Glu Asp Gly Lys Val
        195                 200                 205

Ser Leu Ile Ser Ile Asp Gly Leu His Gln Leu His Ile Leu Ile Phe
    210                 215                 220

Phe Leu Ala Val Phe His Val Leu Phe Ser Val Ile Thr Met Thr Leu
225                 230                 235                 240

Gly Arg Ile Lys Ile Arg Gly Trp Lys Glu Trp Glu Gln Glu Thr Ser
                245                 250                 255

Thr His Asn Tyr Glu Phe Phe Asn Asp Pro Ala Arg Phe Arg Leu Thr
            260                 265                 270

His Glu Thr Ser Phe Val Lys Ala His Thr Ser Phe Trp Thr Arg Leu
        275                 280                 285

Pro Phe Phe Phe Tyr Ile Ser Cys Phe Phe Arg Gln Phe Tyr Gly Ser
    290                 295                 300

Val Ser Lys Ala Asp Tyr Leu Thr Leu Arg Asn Gly Phe Ile Thr Val
305                 310                 315                 320

His Leu Ala Pro Gly Ser Lys Phe Asn Phe Gln Arg Tyr Ile Lys Arg
                325                 330                 335

Ser Leu Glu Asp Asp Phe Lys Val Val Val Gly Val Ser Pro Phe Leu
            340                 345                 350

Trp Ser Ser Phe Val Ile Phe Leu Leu Leu Asn Leu Ser Gly Trp His
        355                 360                 365

Thr Leu Phe Trp Ala Ser Phe Ile Pro Leu Leu Ile Ile Leu Ala Val
    370                 375                 380

Gly Ser Lys Leu Gln Ala Ile Leu Thr Arg Met Ala Leu Glu Ile Ser
385                 390                 395                 400

Glu Lys His Ala Val Val Gln Gly Ile Pro Leu Val Gln Gly Ser Asp
                405                 410                 415

Lys Tyr Phe Trp Phe Gly Arg Pro Gln Leu Ile Leu His Leu Met His
            420                 425                 430

Phe Ser Leu Phe Gln Asn Ala Phe Gln Thr Thr Tyr Ile Leu Ser Thr
        435                 440                 445

Leu Tyr Ser Phe Gly Leu Asn Ser Cys Phe Phe Asp Gly His Ile Leu
    450                 455                 460

Thr Ile Ile Lys Val Gly Leu Gly Val Val Ala Leu Phe Leu Cys Ser
465                 470                 475                 480

Tyr Val Thr Leu Pro Ile Tyr Ala Leu Val Asn Gln Met Gly Ser Gly
                485                 490                 495

Met Lys Arg Ser Ile Phe Asp Glu Gln Thr Ser Lys Ala Leu Met Lys
            500                 505                 510

Trp Gln Glu Thr Ala Lys Lys Lys Arg Ala Lys Arg Ala Ser Ala Thr
        515                 520                 525

Lys Thr Leu Gly Gly Ser Ser Asn Ala Ser Pro Leu His Ser Leu Arg
    530                 535                 540

Arg Phe Lys Thr Thr Gly His Ser Ile Arg Val Pro Thr Tyr Glu Asp
545                 550                 555                 560

Leu Glu Ser Ser Asp Tyr Glu Gly Asp Pro Leu Ala Thr Pro Thr Gln
                565                 570                 575

Ala Ser Thr Ser Glu Ser Ile Asn Val Asp Val Lys Asp Gly Asp Glu
            580                 585                 590

Ile Gln Gln Ile Ala Glu Thr Glu Gln Pro His Ser Thr Ile Gln Thr
        595                 600                 605

Lys Glu Gly Asp Glu Phe Ser Phe Ile Lys Pro Ala Thr Leu Gly
```

610 615 620

<210> SEQ ID NO 15
<211> LENGTH: 1662
<212> TYPE: DNA
<213> ORGANISM: Cucumis sativus

<400> SEQUENCE: 15

```
atggctgaaa atgaacagga gactcgatct ttggctttga ctcccacttg gtctgttgct     60
tctgtgctga ctattttcgt tgcagtctct ttgcttgtgg agcggtccat tcaccggtta    120
agcacttggt tggggaaacc taatcgaaag ccactgtttg aggcagtgga gaaaatgaaa    180
gaagagttga tgctgcttgg atttatttct ctccttttaa cagctacttc aagctcaata    240
tcaaatatct gcgttccatc aaagttctac aataccccctt ttactccatg caccagagct    300
gaggctgacg aacatgaaga tgacaattca tccgaggaac ggaaactata tacagcttct    360
gtattacccc atttgtttag gcggatgctt aatgtgaata agaaaacctg caaagagggt    420
tatgagccgt ttgtttcata tgagggtctt gagcaattgc atcgctttat ctttataatg    480
gcagtaactc atatatctta tagctgctta acaatgttac tcgcaattgt gaagattcac    540
agatggaggg tttgggagaa tgaagcccat atggacagac atgattcact aaatgatatc    600
acaagagaaa tgacgttgcg gaggcaatca acctttgttc gatatcacac ttcaaatcct    660
atgacaagga acagtttct aatctgggtg acatgttttt tccggcaatt tgggaattct    720
gtagttcgtg ctgactacct cacacttcgc aagggcttca tcatgaatca tcatctcccc    780
ttgacttatg atttccacag ttacatgatt cgctccatgg aagaagaatt ccaaaggata    840
gttggcgtga gtggtccgtt gtggggattt gtcgttgctt tcatgctgtt taatgtaaaa    900
ggctctaatc tgtatttctg gatagcaagc gttcctattg ctcttgttct tttagtgggc    960
acgaagctgc aacatgtaat tgcaacattg gcattggaaa gtgctggtat aactggttca   1020
ttttcgggtt caaagctaaa gccaagagat gatcttttct ggtttaagaa gcctgaactc   1080
cttttgtcct taatccactt tatccttttc cagaatgcat ttgagttggc atcattcttc   1140
tggttctggt ggcaattcgg atataattct tgctttatca ggaatcatat gcttgtctat   1200
gcaagacttg ttttgggatt cgctgggcag ttcctttgca gctacagcac cttgcccttg   1260
tatgctttgg ttactcagat gggaacaaac tataaagctg cattaattcc acaaagaata   1320
agggaaacaa tccatggatg gggaaggca gctagaagga aaagaaggct ccgcatgttt   1380
gcagatgaca ccacgattca cactgaaaca agcacggtga tgtcacttga ggatgatgac   1440
cgtaggctta ttgatgatat ttctgaaact actgccgact acacgtcaat cgaactacag   1500
ccgacttctg tacacgatga acctgactct gttcctaatg aacgaccaag cagagctaga   1560
acgcctcttc tacaaccctc cacatctctt tctgcatcag ttgatcataa gtttgaggta   1620
gaaaacttta tgaggagctt ttctatgcca gtaaaaagat ag                       1662
```

<210> SEQ ID NO 16
<211> LENGTH: 553
<212> TYPE: PRT
<213> ORGANISM: Cucumis sativus

<400> SEQUENCE: 16

```
Met Ala Glu Asn Glu Gln Glu Thr Arg Ser Leu Ala Leu Thr Pro Thr
1               5                   10                  15

Trp Ser Val Ala Ser Val Leu Thr Ile Phe Val Ala Val Ser Leu Leu
            20                  25                  30
```

```
Val Glu Arg Ser Ile His Arg Leu Ser Thr Trp Leu Gly Lys Pro Asn
        35                  40                  45

Arg Lys Pro Leu Phe Glu Ala Val Glu Lys Met Lys Glu Glu Leu Met
    50                  55                  60

Leu Leu Gly Phe Ile Ser Leu Leu Leu Thr Ala Thr Ser Ser Ser Ile
65                  70                  75                  80

Ser Asn Ile Cys Val Pro Ser Lys Phe Tyr Asn Thr Pro Phe Thr Pro
                85                  90                  95

Cys Thr Arg Ala Glu Ala Asp Glu His Glu Asp Asp Asn Ser Ser Glu
            100                 105                 110

Glu Arg Lys Leu Tyr Thr Ala Ser Val Leu Pro His Leu Phe Arg Arg
        115                 120                 125

Met Leu Asn Val Asn Lys Lys Thr Cys Lys Glu Gly Tyr Glu Pro Phe
    130                 135                 140

Val Ser Tyr Glu Gly Leu Glu Gln Leu His Arg Phe Ile Phe Ile Met
145                 150                 155                 160

Ala Val Thr His Ile Ser Tyr Ser Cys Leu Thr Met Leu Leu Ala Ile
                165                 170                 175

Val Lys Ile His Arg Trp Arg Val Trp Glu Asn Glu Ala His Met Asp
            180                 185                 190

Arg His Asp Ser Leu Asn Asp Ile Thr Arg Glu Met Thr Leu Arg Arg
        195                 200                 205

Gln Ser Thr Phe Val Arg Tyr His Thr Ser Asn Pro Met Thr Arg Asn
    210                 215                 220

Ser Phe Leu Ile Trp Val Thr Cys Phe Phe Arg Gln Phe Gly Asn Ser
225                 230                 235                 240

Val Val Arg Ala Asp Tyr Leu Thr Leu Arg Lys Gly Phe Ile Met Asn
                245                 250                 255

His His Leu Pro Leu Thr Tyr Asp Phe His Ser Tyr Met Ile Arg Ser
            260                 265                 270

Met Glu Glu Glu Phe Gln Arg Ile Val Gly Val Ser Gly Pro Leu Trp
        275                 280                 285

Gly Phe Val Val Ala Phe Met Leu Phe Asn Val Lys Gly Ser Asn Leu
    290                 295                 300

Tyr Phe Trp Ile Ala Ser Val Pro Ile Ala Leu Val Leu Leu Val Gly
305                 310                 315                 320

Thr Lys Leu Gln His Val Ile Ala Thr Leu Ala Leu Glu Ser Ala Gly
                325                 330                 335

Ile Thr Gly Ser Phe Ser Gly Ser Lys Leu Lys Pro Arg Asp Asp Leu
            340                 345                 350

Phe Trp Phe Lys Lys Pro Glu Leu Leu Leu Ser Leu Ile His Phe Ile
        355                 360                 365

Leu Phe Gln Asn Ala Phe Glu Leu Ala Ser Phe Phe Trp Phe Trp Trp
    370                 375                 380

Gln Phe Gly Tyr Asn Ser Cys Phe Ile Arg Asn His Met Leu Val Tyr
385                 390                 395                 400

Ala Arg Leu Val Leu Gly Phe Ala Gly Gln Phe Leu Cys Ser Tyr Ser
                405                 410                 415

Thr Leu Pro Leu Tyr Ala Leu Val Thr Gln Met Gly Thr Asn Tyr Lys
            420                 425                 430

Ala Ala Leu Ile Pro Gln Arg Ile Arg Glu Thr Ile His Gly Trp Gly
        435                 440                 445
```

```
Lys Ala Ala Arg Arg Lys Arg Arg Leu Arg Met Phe Ala Asp Asp Thr
    450                 455                 460

Thr Ile His Thr Glu Thr Ser Thr Val Met Ser Leu Glu Asp Asp Asp
465                 470                 475                 480

Arg Arg Leu Ile Asp Asp Ile Ser Glu Thr Thr Ala Asp Tyr Thr Ser
                485                 490                 495

Ile Glu Leu Gln Pro Thr Ser Val His Asp Glu Pro Asp Ser Val Pro
            500                 505                 510

Asn Glu Arg Pro Ser Arg Ala Arg Thr Pro Leu Leu Gln Pro Ser Thr
        515                 520                 525

Ser Leu Ser Ala Ser Val Asp His Lys Phe Glu Val Glu Asn Phe Met
    530                 535                 540

Arg Ser Phe Ser Met Pro Val Lys Arg
545                 550


<210> SEQ ID NO 17
<211> LENGTH: 1587
<212> TYPE: DNA
<213> ORGANISM: Cucumis sativus

<400> SEQUENCE: 17

atggaagaag aaggacgatc cttggccgtt acccccactt gggcttttgc cacagtggtc     60

actctcatgg tttctcttgg attcttcttc caaggcacgt tgaaacggac caaaaagtgg    120

ttgaatagga cgaaragaaa atcgttactt gctgcgttgg agaagattaa agaagagctg    180

atgctctttg gacttctttc gttgttgatg ggtcactgga ttgtttttgt tgcaagaatt    240

tgtgtcaagt catctgtctt gagcagccgt ttctatcctt gtgcgttgga gactgatctg    300

aaacgagtta gacatatttt cattgcaact caaagcttga acagttctgt tccaagggag    360

cacaataacg atgggatacg agagtattgt cctgagggtc gtgaatcgtt tgcttcatat    420

gaaagtttag agcagcttca tcgactaata ttcgttctcg gtgtcaccca tgtttcatat    480

agcttcattg ccattgccct ggctatgatt aagatatatg gctggaggac gtgggaaaat    540

gaggctaagg ctttggccat tcgaaacgcc gaagaagaat ctgcacaagc accatcaact    600

ggaccaaaca taaggcgact atcaactttt atctttcacc atacttctca tccatggagt    660

cagcatagag tccttgtttg gctgctctgt ttcagccgcc agttttggag ttctattaat    720

cgagctgatt acatggcttt gcggttggga tttatcagta ctcatgaact tcctatatcg    780

tatgacttcc acaattatat gcttcgaagc atggatgatg aatttcgtga tatggttggt    840

ataagtgtac cactctggat atatgccatt gcttgcatct tcctcaactt ccatggaagc    900

aacatttaca tttggctttc ctttgtccct gcaattgtgg taaagctagc tgtagaagtt    960

gtggattcat ccccaagggg atattattgt tttaacttga gagatgagct gttttggttt   1020

gggaagccta agcttctttt atggttgata caatttatat ccttccagaa tgcttttgag   1080

atggctacat tcatttggtc cctgtttcag tgggaaatta aggagccttc ttgtttcatg   1140

gataacgaaa cctatgttgg tatccgcttg gcgtttgggg ttatcactca attttggtgt   1200

agcttcatca cattcccact ctatgttata gtaactcaga tggggtcaaa agtcaagaaa   1260

tcacttgtgt cggagaatgt tcgaaactca cttcatcaat ggaaaagaag agtgaaggca   1320

aggccaggtg cttcttcaac ggttacactt gcgggtgcaa catcactttc atcctctgtt   1380

tttacaatgg atgatgaggg tgaagtgacc gacgacttta ccacgaactg ctcggaagga   1440

agcacatcaa atgctgctca atgcacacat ttcccccagt taattcagcc agttttgtca   1500
```

```
gatgacacgg aagtagaaat atctgttagt tctaattctc cacacattag ttccaacgac   1560

agaagtgaag gcaatgggga tggttga                                       1587


<210> SEQ ID NO 18
<211> LENGTH: 528
<212> TYPE: PRT
<213> ORGANISM: Cucumis sativus

<400> SEQUENCE: 18

Met Glu Glu Glu Gly Arg Ser Leu Ala Val Thr Pro Thr Trp Ala Phe
1               5                   10                  15

Ala Thr Val Val Thr Leu Met Val Ser Leu Gly Phe Phe Phe Gln Gly
            20                  25                  30

Thr Leu Lys Arg Thr Lys Lys Trp Leu Asn Arg Thr Lys Arg Lys Ser
        35                  40                  45

Leu Leu Ala Ala Leu Glu Lys Ile Lys Glu Glu Leu Met Leu Phe Gly
    50                  55                  60

Leu Leu Ser Leu Leu Met Gly His Trp Ile Val Phe Val Ala Arg Ile
65                  70                  75                  80

Cys Val Lys Ser Ser Val Leu Ser Ser Arg Phe Tyr Pro Cys Ala Leu
                85                  90                  95

Glu Thr Asp Leu Lys Arg Val Arg His Ile Phe Ile Ala Thr Gln Ser
            100                 105                 110

Leu Asn Ser Ser Val Pro Arg Glu His Asn Asn Asp Gly Ile Arg Glu
        115                 120                 125

Tyr Cys Pro Glu Gly Arg Glu Ser Phe Ala Ser Tyr Glu Ser Leu Glu
    130                 135                 140

Gln Leu His Arg Leu Ile Phe Val Leu Gly Val Thr His Val Ser Tyr
145                 150                 155                 160

Ser Phe Ile Ala Ile Ala Leu Ala Met Ile Lys Ile Tyr Gly Trp Arg
                165                 170                 175

Thr Trp Glu Asn Glu Ala Lys Ala Leu Ala Ile Arg Asn Ala Glu Glu
            180                 185                 190

Glu Ser Ala Gln Ala Pro Ser Thr Gly Pro Asn Ile Arg Arg Leu Ser
        195                 200                 205

Thr Phe Ile Phe His His Thr Ser His Pro Trp Ser Gln His Arg Val
    210                 215                 220

Leu Val Trp Leu Leu Cys Phe Ser Arg Gln Phe Trp Ser Ser Ile Asn
225                 230                 235                 240

Arg Ala Asp Tyr Met Ala Leu Arg Leu Gly Phe Ile Ser Thr His Glu
                245                 250                 255

Leu Pro Ile Ser Tyr Asp Phe His Asn Tyr Met Leu Arg Ser Met Asp
            260                 265                 270

Asp Glu Phe Arg Asp Met Val Gly Ile Ser Val Pro Leu Trp Ile Tyr
        275                 280                 285

Ala Ile Ala Cys Ile Phe Leu Asn Phe His Gly Ser Asn Ile Tyr Ile
    290                 295                 300

Trp Leu Ser Phe Val Pro Ala Ile Val Val Lys Leu Ala Val Glu Val
305                 310                 315                 320

Val Asp Ser Ser Pro Arg Gly Tyr Tyr Cys Phe Asn Leu Arg Asp Glu
                325                 330                 335

Leu Phe Trp Phe Gly Lys Pro Lys Leu Leu Leu Trp Leu Ile Gln Phe
            340                 345                 350

Ile Ser Phe Gln Asn Ala Phe Glu Met Ala Thr Phe Ile Trp Ser Leu
```

-continued

```
        355                 360                 365

Phe Gln Trp Glu Ile Lys Glu Pro Ser Cys Phe Met Asp Asn Glu Thr
    370                 375                 380

Tyr Val Gly Ile Arg Leu Ala Phe Gly Val Ile Thr Gln Phe Trp Cys
385                 390                 395                 400

Ser Phe Ile Thr Phe Pro Leu Tyr Val Ile Val Thr Gln Met Gly Ser
                405                 410                 415

Lys Val Lys Lys Ser Leu Val Ser Glu Asn Val Arg Asn Ser Leu His
            420                 425                 430

Gln Trp Lys Arg Arg Val Lys Ala Arg Pro Gly Ala Ser Ser Thr Val
        435                 440                 445

Thr Leu Ala Gly Ala Thr Ser Leu Ser Ser Ser Val Phe Thr Met Asp
    450                 455                 460

Asp Glu Gly Glu Val Thr Asp Asp Phe Thr Thr Asn Cys Ser Glu Gly
465                 470                 475                 480

Ser Thr Ser Asn Ala Ala Gln Cys Thr His Phe Pro Gln Leu Ile Gln
                485                 490                 495

Pro Val Leu Ser Asp Asp Thr Glu Val Glu Ile Ser Val Ser Ser Asn
            500                 505                 510

Ser Pro His Ile Ser Ser Asn Asp Arg Ser Glu Gly Asn Gly Asp Gly
        515                 520                 525


<210> SEQ ID NO 19
<211> LENGTH: 1707
<212> TYPE: DNA
<213> ORGANISM: Cucumis sativus

<400> SEQUENCE: 19

atggctgaaa atgcctccca ggagggaaga tctctggctc tgacgcctac ttggtctgtt     60

gcttccgtgt tgaccattct cgtcgcagtt tcattgcttg tagaacgctc cattcatagg    120

ctaagctctt ggctgggaaa aactcataga aaacccttat ttgaggcagt ggagaaaatg    180

aaagaagagt taatgctgct tggttttatt tctttgcttc tgacggcaac atcaagtcta    240

atatcaaata tctgcattcc atccaagttt tatgatacat cttttattcc gtgctctcag    300

tcggagattg atgaacaaaa tgcggataat tcttcatctg agaagcgaaa gctatttatg    360

gtttctgttt tcccacattt gaataggagg atgctaactg tgaacaaaaa tacatgcaaa    420

gagggtcatg agccctttgt ttcctatgag ggacttgagc aattgcatcg ctttatcttt    480

gtgatggcag ttactcatat ttcttatagt tgcttaacca tgttgttggc aattgtgaag    540

atccacagtt ggagagaatg ggaaaatgaa gctcacatgg accaccatga tttattcaac    600

gatacaacga aaaaaaagat aatgcagaga caatctacct ttgtacaata tcacgcctcc    660

aatcctttaa ccaggaatag ctttcttatc tggatgacct gtttcttcag gcaatttggg    720

cgttctgttg ttcgttctga ctaccttaca cttcgcaaag gcttcatcac gaatcacaac    780

ctctcatcaa aatatgattt ccatagctac atggttcgtt ctatggaaga agaattccag    840

agaatagttg gtgtgagtgg tccgttatgr ggatttgtcg tagctttttt gctatttaat    900

gtgaaaggct ccaaccttta cttttggata gcaactattc ctgttactct tgttctttta    960

gtgggcacaa agttacagca tgttattgca actttgacgt tggagaatgc tggtataacc   1020

ggattctttt ctggagcaaa gctgaggccc cgtgatgatc ttttctggtt taagaagcct   1080

gaacttctgt tgtccttgat ccattttgtt cttttccaga atgctttcga attggcttcg   1140

ttcttctggt tctggtggca atctggatgt agttcttgct tcattagcaa tcatctgctt   1200
```

```
gtctatgtaa gactaatctt gggttttgct ggacaatttc tttgcagcta tagcacctwr   1260

cccytatacg cactggttac tcagatggga acaaactaca aggctgcctt aattcctcaa   1320

agaataaggg aaacaatcca tgggtggggt aagtcagcta gaaggaagag aaggctccgg   1380

atatttactg atgatgccac aatccacacg gaaacaagca ccgtgatgtc actkgaggac   1440

gatgacaacc aacatgtwga tacacctaaa gctgcaactg gctatgccat aattgagatg   1500

cagccaccta ctgcagcaaa tgtgtccgcc tctgtttcta atgatgcatc acgtgcggtt   1560

agaactcccc ttcttcagcc ctctctgtct ctttcattgc cwgtggctca aaacttcaat   1620

gacggagccc ctttaagaag ctcatcaatg ccggctcaaa ayttcgatgc cgaaaactct   1680

ttaagaagct catctatgcc gagataa                                       1707
```

<210> SEQ ID NO 20
<211> LENGTH: 568
<212> TYPE: PRT
<213> ORGANISM: Cucumis sativus

<400> SEQUENCE: 20

```
Met Ala Glu Asn Ala Ser Gln Glu Gly Arg Ser Leu Ala Leu Thr Pro
1               5                   10                  15

Thr Trp Ser Val Ala Ser Val Leu Thr Ile Leu Val Ala Val Ser Leu
            20                  25                  30

Leu Val Glu Arg Ser Ile His Arg Leu Ser Ser Trp Leu Gly Lys Thr
        35                  40                  45

His Arg Lys Pro Leu Phe Glu Ala Val Glu Lys Met Lys Glu Glu Leu
    50                  55                  60

Met Leu Leu Gly Phe Ile Ser Leu Leu Leu Thr Ala Thr Ser Ser Leu
65                  70                  75                  80

Ile Ser Asn Ile Cys Ile Pro Ser Lys Phe Tyr Asp Thr Ser Phe Ile
                85                  90                  95

Pro Cys Ser Gln Ser Glu Ile Asp Glu Gln Asn Ala Asp Asn Ser Ser
            100                 105                 110

Ser Glu Lys Arg Lys Leu Phe Met Val Ser Val Phe Pro His Leu Asn
        115                 120                 125

Arg Arg Met Leu Thr Val Asn Lys Asn Thr Cys Lys Glu Gly His Glu
    130                 135                 140

Pro Phe Val Ser Tyr Glu Gly Leu Glu Gln Leu His Arg Phe Ile Phe
145                 150                 155                 160

Val Met Ala Val Thr His Ile Ser Tyr Ser Cys Leu Thr Met Leu Leu
                165                 170                 175

Ala Ile Val Lys Ile His Ser Trp Arg Glu Trp Glu Asn Glu Ala His
            180                 185                 190

Met Asp His His Asp Leu Phe Asn Asp Thr Thr Lys Lys Lys Ile Met
        195                 200                 205

Gln Arg Gln Ser Thr Phe Val Gln Tyr His Ala Ser Asn Pro Leu Thr
    210                 215                 220

Arg Asn Ser Phe Leu Ile Trp Met Thr Cys Phe Phe Arg Gln Phe Gly
225                 230                 235                 240

Arg Ser Val Val Arg Ser Asp Tyr Leu Thr Leu Arg Lys Gly Phe Ile
                245                 250                 255

Thr Asn His Asn Leu Ser Ser Lys Tyr Asp Phe His Ser Tyr Met Val
            260                 265                 270

Arg Ser Met Glu Glu Glu Phe Gln Arg Ile Val Gly Val Ser Gly Pro
```

```
        275                 280                 285

Leu Trp Gly Phe Val Val Ala Phe Leu Leu Phe Asn Val Lys Gly Ser
    290                 295                 300

Asn Leu Tyr Phe Trp Ile Ala Thr Ile Pro Val Thr Leu Val Leu Leu
305                 310                 315                 320

Val Gly Thr Lys Leu Gln His Val Ile Ala Thr Leu Thr Leu Glu Asn
                325                 330                 335

Ala Gly Ile Thr Gly Phe Phe Ser Gly Ala Lys Leu Arg Pro Arg Asp
            340                 345                 350

Asp Leu Phe Trp Phe Lys Lys Pro Glu Leu Leu Leu Ser Leu Ile His
        355                 360                 365

Phe Val Leu Phe Gln Asn Ala Phe Glu Leu Ala Ser Phe Phe Trp Phe
    370                 375                 380

Trp Trp Gln Ser Gly Cys Ser Ser Cys Phe Ile Ser Asn His Leu Leu
385                 390                 395                 400

Val Tyr Val Arg Leu Ile Leu Gly Phe Ala Gly Gln Phe Leu Cys Ser
                405                 410                 415

Tyr Ser Thr Leu Pro Leu Tyr Ala Leu Val Thr Gln Met Gly Thr Asn
            420                 425                 430

Tyr Lys Ala Ala Leu Ile Pro Gln Arg Ile Arg Glu Thr Ile His Gly
        435                 440                 445

Trp Gly Lys Ser Ala Arg Arg Lys Arg Arg Leu Arg Ile Phe Thr Asp
    450                 455                 460

Asp Ala Thr Ile His Thr Glu Thr Ser Thr Val Met Ser Leu Glu Asp
465                 470                 475                 480

Asp Asp Asn Gln His Val Asp Thr Pro Lys Ala Ala Thr Gly Tyr Ala
                485                 490                 495

Ile Ile Glu Met Gln Pro Pro Thr Ala Ala Asn Val Ser Ala Ser Val
            500                 505                 510

Ser Asn Asp Ala Ser Arg Ala Val Arg Thr Pro Leu Leu Gln Pro Ser
        515                 520                 525

Leu Ser Leu Ser Leu Pro Val Ala Gln Asn Phe Asn Asp Gly Ala Pro
    530                 535                 540

Leu Arg Ser Ser Ser Met Pro Ala Gln Asn Phe Asp Ala Glu Asn Ser
545                 550                 555                 560

Leu Arg Ser Ser Ser Met Pro Arg
                565
```

```
<210> SEQ ID NO 21
<211> LENGTH: 1671
<212> TYPE: DNA
<213> ORGANISM: Cucumis sativus

<400> SEQUENCE: 21

atggaacttc aaggaggaag gtcactggct gaaacgccta cctactcggt tgcttctgtg      60

gttactgtca tggtctttgt cagcttggtg gtggagcggg caatctatag gtttggaaag     120

tggttgaaga araccaagag aaaggctctg tttgcttctt tggagaarat taaggaagag     180

ctgatgctgc ttggactgat atctttgatg ctggcacaat gtgcaaggtg gatatctgaa     240

atttgtgtga actcgtccct tttcaccagt agattctaca tttgttcaga agaagattat     300

gccaccaatg aacatattct gcttgaaagt tctctattgt ctcataatga aattgtcatt     360

cctcaaagag aattaagtgc tcttccgcat caatgtggtg agggtcgtga gccttttgtt     420

tcatatgagg gacttgaaca acttcaccgg ttcttgttcg ttcttgggat cactcatgtt     480
```

```
ctttatagct gtctagctgt tggtctggca atgagtaaga tatacagttg gaggaaatgg    540

gaaagtcaag ttaaattagc tgctgaagat aatttaccag ctaaaagaaa taaggtcatg    600

aggcggcaaa cgacgtttgt tttccatcac acatctcatc catggagcag gagtcgtatt    660

ctcatatgga tgctttgttt cctacgtcag ttcaagagtt cgataaagaa atcagactat    720

ttggccctcc gtttgggttt cattacaaag cacaaattac cgatctctta tgatttccac    780

aagtacatgg ttcggagcat ggaagacgag ttccatggaa tccttggaat tagctggccg    840

ctatggggct acgccattct ktgcatcttt gtcaacattc acggtttaaa tatctacttt    900

tggctatctt tcataccggc tgctctwgtt atgctcgttg ggacaaaact tcaacaygtw    960

gtatcctctt tggctcttga agtwttggaa cagagaggtg ggattcaaat aaaaccaaga   1020

gacgatctgt tttggtttgg aaagcctgtg attttactmc ggttaataca gctcatcata   1080

tttcagaatg catttgagat ggcgacattt atmtggtcct tgtggggatt taaggaaaga   1140

tcttgcttcg tgaagaacga ctttatgata atcacgaggt tgacttcagg tgttcttgta   1200

cagttttggt gcagctatag cattgtgcca cttaatataa ttgttacaca gatgggatcc   1260

aagtgtaaga aagcattggt ggctgagagc gtgagagagt cattgcatag ttggtgcaag   1320

agagtaaagg agaggtccaa acgwgactct gcacattcca tcactacaag atcagtatgt   1380

tcacttgaat caatggttga tgaacgagat gaaataacca ttgcttccgg tacgttgtca   1440

cggagctcat cttttgagac ctcaaatcag gtgaccgtac aatctactgc ccaactagag   1500

gctattattg agtcttcaag cttaaggagg catgaagaac ttccccccac catggcggat   1560

tttctatcac aatctgcaag agtttctcat gctaatggcc tagaaaataa tgcagagagt   1620

ggcgaagata gcaaggtcga gtcacttttc gacttgttca aaaggacatg a            1671
```

<210> SEQ ID NO 22
<211> LENGTH: 556
<212> TYPE: PRT
<213> ORGANISM: Cucumis sativus

<400> SEQUENCE: 22

```
Met Glu Leu Gln Gly Gly Arg Ser Leu Ala Glu Thr Pro Thr Tyr Ser
1               5                   10                  15

Val Ala Ser Val Val Thr Val Met Val Phe Val Ser Leu Val Val Glu
            20                  25                  30

Arg Ala Ile Tyr Arg Phe Gly Lys Trp Leu Lys Lys Thr Lys Arg Lys
        35                  40                  45

Ala Leu Phe Ala Ser Leu Glu Lys Ile Lys Glu Glu Leu Met Leu Leu
    50                  55                  60

Gly Leu Ile Ser Leu Met Leu Ala Gln Cys Ala Arg Trp Ile Ser Glu
65                  70                  75                  80

Ile Cys Val Asn Ser Ser Leu Phe Thr Ser Arg Phe Tyr Ile Cys Ser
                85                  90                  95

Glu Glu Asp Tyr Ala Thr Asn Glu His Ile Leu Leu Glu Ser Ser Leu
            100                 105                 110

Leu Ser His Asn Glu Ile Val Ile Pro Gln Arg Glu Leu Ser Ala Leu
        115                 120                 125

Pro His Gln Cys Gly Glu Gly Arg Glu Pro Phe Val Ser Tyr Glu Gly
    130                 135                 140

Leu Glu Gln Leu His Arg Phe Leu Phe Val Leu Gly Ile Thr His Val
145                 150                 155                 160
```

```
Leu Tyr Ser Cys Leu Ala Val Gly Leu Ala Met Ser Lys Ile Tyr Ser
                165                 170                 175

Trp Arg Lys Trp Glu Ser Gln Val Lys Leu Ala Ala Glu Asp Asn Leu
            180                 185                 190

Pro Ala Lys Arg Asn Lys Val Met Arg Arg Gln Thr Thr Phe Val Phe
        195                 200                 205

His His Thr Ser His Pro Trp Ser Arg Ser Arg Ile Leu Ile Trp Met
    210                 215                 220

Leu Cys Phe Leu Arg Gln Phe Lys Ser Ser Ile Lys Lys Ser Asp Tyr
225                 230                 235                 240

Leu Ala Leu Arg Leu Gly Phe Ile Thr Lys His Lys Leu Pro Ile Ser
                245                 250                 255

Tyr Asp Phe His Lys Tyr Met Val Arg Ser Met Glu Asp Glu Phe His
            260                 265                 270

Gly Ile Leu Gly Ile Ser Trp Pro Leu Trp Gly Tyr Ala Ile Leu Cys
        275                 280                 285

Ile Phe Val Asn Ile His Gly Leu Asn Ile Tyr Phe Trp Leu Ser Phe
    290                 295                 300

Ile Pro Ala Ala Leu Val Met Leu Val Gly Thr Lys Leu Gln His Val
305                 310                 315                 320

Val Ser Ser Leu Ala Leu Glu Val Leu Glu Gln Arg Gly Gly Ile Gln
                325                 330                 335

Ile Lys Pro Arg Asp Asp Leu Phe Trp Phe Gly Lys Pro Val Ile Leu
            340                 345                 350

Leu Arg Leu Ile Gln Leu Ile Ile Phe Gln Asn Ala Phe Glu Met Ala
        355                 360                 365

Thr Phe Ile Trp Ser Leu Trp Gly Phe Lys Glu Arg Ser Cys Phe Val
    370                 375                 380

Lys Asn Asp Phe Met Ile Ile Thr Arg Leu Thr Ser Gly Val Leu Val
385                 390                 395                 400

Gln Phe Trp Cys Ser Tyr Ser Ile Val Pro Leu Asn Ile Ile Val Thr
                405                 410                 415

Gln Met Gly Ser Lys Cys Lys Lys Ala Leu Val Ala Glu Ser Val Arg
            420                 425                 430

Glu Ser Leu His Ser Trp Cys Lys Arg Val Lys Glu Arg Ser Lys Arg
        435                 440                 445

Asp Ser Ala His Ser Ile Thr Thr Arg Ser Val Cys Ser Leu Glu Ser
    450                 455                 460

Met Val Asp Glu Arg Asp Glu Ile Thr Ile Ala Ser Gly Thr Leu Ser
465                 470                 475                 480

Arg Ser Ser Ser Phe Glu Thr Ser Asn Gln Val Thr Val Gln Ser Thr
                485                 490                 495

Ala Gln Leu Glu Ala Ile Ile Glu Ser Ser Ser Leu Arg Arg His Glu
            500                 505                 510

Glu Leu Pro Pro Thr Met Ala Asp Phe Leu Ser Gln Ser Ala Arg Val
        515                 520                 525

Ser His Ala Asn Gly Leu Glu Asn Asn Ala Glu Ser Gly Glu Asp Ser
    530                 535                 540

Lys Val Glu Ser Leu Phe Asp Leu Phe Lys Arg Thr
545                 550                 555
```

<210> SEQ ID NO 23
<211> LENGTH: 20
<212> TYPE: DNA

```
<213> ORGANISM: Artificial Sequence
<220> FEATURE:
<223> OTHER INFORMATION: CsKIP2 specific PCR primer ID1

<400> SEQUENCE: 23

cgacacttga gcttctggag                                                20


<210> SEQ ID NO 24
<211> LENGTH: 22
<212> TYPE: DNA
<213> ORGANISM: Artificial Sequence
<220> FEATURE:
<223> OTHER INFORMATION: CsKIP2 specific PCR Primer ID2

<400> SEQUENCE: 24

gcaagatgtg caacaatgaa tc                                             22


<210> SEQ ID NO 25
<211> LENGTH: 23
<212> TYPE: DNA
<213> ORGANISM: Artificial Sequence
<220> FEATURE:
<223> OTHER INFORMATION: CsKIP 2 specific PCR Primer ID3

<400> SEQUENCE: 25

cccgcaatgt ggctatttgc tgt                                            23


<210> SEQ ID NO 26
<211> LENGTH: 20
<212> TYPE: DNA
<213> ORGANISM: Artificial Sequence
<220> FEATURE:
<223> OTHER INFORMATION: CsKIP2 specific PCR Primer ID4

<400> SEQUENCE: 26

cccgaggctg aacgaccgga                                                20


<210> SEQ ID NO 27
<211> LENGTH: 199
<212> TYPE: DNA
<213> ORGANISM: Cucumis sativus

<400> SEQUENCE: 27

cccgcaatgt ggctatttgc tgttctcttc atcctaacca atacaaatgg gtggtattca     60

tatctatggc tgcctttcat ctccttaatt ataattctat tggtgggaac aaagctccat    120

gttattaaaa ctcatatggg attgacaatt caagaaaggg gtcatgttgt gaagggtgtt    180

ccggtcgttc acgctcggg                                                199


<210> SEQ ID NO 28
<211> LENGTH: 127
<212> TYPE: DNA
<213> ORGANISM: Cucumis sativus

<400> SEQUENCE: 28

cccgcaatgt ggctatttgc tgttctcttc atcctaacca atacaaatgg gtggtattca     60

tatctatggc tgcctttcat ctccttaatt ataattctat tgggtgttcc ggtcgttcag    120

cctcggg                                                             127


<210> SEQ ID NO 29
<211> LENGTH: 593
<212> TYPE: PRT
<213> ORGANISM: Cucumis sativus
```

<400> SEQUENCE: 29

```
Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gln Ser Leu Ile Thr
65                  70                  75                  80

Asn Val Cys Ile Pro Pro Asp Val Ala Ala Thr Trp His Pro Cys Ser
                85                  90                  95

Pro Gln Arg Glu Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160

His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asn Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
```

```
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495

Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
            580                 585                 590

Val


<210> SEQ ID NO 30
<211> LENGTH: 593
<212> TYPE: PRT
<213> ORGANISM: Cucumis sativus

<400> SEQUENCE: 30

Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gln Ser Leu Ile Thr
65                  70                  75                  80

Asn Val Cys Ile Pro Pro Asp Val Ala Ala Thr Trp His Pro Cys Ser
                85                  90                  95

Pro Gln Arg Glu Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160

His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
```

```
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asp Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495

Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
            580                 585                 590

Val
```

```
<210> SEQ ID NO 31
<211> LENGTH: 608
<212> TYPE: PRT
<213> ORGANISM: Cucumis sativus

<400> SEQUENCE: 31

Met Leu Phe Tyr Asn Ala Asn Phe Val Gln Lys Ser Arg Leu Phe Gln
1               5                   10                  15

Ala Gly Gly Gly Ala Gly Arg Ser Leu Glu Glu Thr Pro Thr Trp Ala
            20                  25                  30

Val Ala Ala Val Cys Phe Val Leu Val Leu Ile Ser Ile Ile Ile Glu
        35                  40                  45

His Ile Leu His Leu Ile Gly Lys Trp Leu Lys Lys Lys His Lys Arg
    50                  55                  60

Ala Leu Tyr Glu Ala Leu Glu Lys Ile Lys Ser Glu Leu Met Leu Leu
65                  70                  75                  80

Gly Phe Ile Ser Leu Leu Leu Thr Val Gly Gln Ser Leu Ile Thr Asn
                85                  90                  95

Val Cys Ile Pro Pro Asp Val Ala Ala Thr Trp His Pro Cys Ser Pro
            100                 105                 110

Gln Arg Glu Glu Glu Leu Thr Lys Glu Ala Asp Leu Val Asp Ser Asp
        115                 120                 125

Gln Asn Arg Arg Lys Leu Leu Ala Leu Ser His His Val Asn Ala Thr
    130                 135                 140

Phe Arg Arg Ser Leu Ala Ala Ala Gly Gly Thr Asp Lys Cys Ala Ala
145                 150                 155                 160

Lys Gly Lys Val Pro Phe Val Ser Glu Gly Gly Ile His Gln Leu His
                165                 170                 175

Ile Phe Ile Phe Val Leu Ala Val Phe His Val Leu Tyr Cys Val Leu
            180                 185                 190

Thr Leu Ala Leu Gly Asn Ala Lys Met Arg Ser Trp Lys Ser Trp Glu
        195                 200                 205

Lys Glu Thr Arg Thr Val Glu Tyr Gln Phe Ser His Asp Pro Glu Arg
    210                 215                 220

Phe Arg Phe Ala Arg Asp Thr Ser Phe Gly Arg Arg His Leu Ser Phe
225                 230                 235                 240

Trp Thr Lys Ser Pro Phe Leu Ile Trp Ile Val Cys Phe Phe Arg Gln
                245                 250                 255

Phe Val Arg Ser Val Pro Lys Val Asp Tyr Leu Thr Leu Arg His Gly
            260                 265                 270

Phe Val Met Ala His Leu Ala Pro His Ser Asp Gln Lys Phe Asp Phe
        275                 280                 285

Gln Lys Tyr Ile Lys Arg Ser Leu Glu Glu Asp Phe Lys Val Val Val
    290                 295                 300

Ser Ile Ser Pro Pro Ile Trp Phe Phe Ala Val Leu Phe Leu Leu Phe
305                 310                 315                 320

Asn Thr His Gly Trp Arg Ala Tyr Leu Trp Leu Pro Phe Val Pro Leu
                325                 330                 335

Ile Ile Val Leu Leu Val Gly Thr Lys Leu Gln Val Ile Ile Thr Lys
            340                 345                 350

Met Ala Leu Arg Ile Gln Glu Arg Gly Glu Val Val Lys Gly Val Pro
        355                 360                 365

Val Val Glu Pro Gly Asp Asp Leu Phe Trp Phe Asn Arg Pro Arg Leu
    370                 375                 380
```

```
Ile Leu Tyr Leu Ile Asn Phe Val Leu Phe Gln Asn Ala Phe Gln Leu
385                 390                 395                 400

Ala Phe Phe Ala Trp Thr Trp Lys Glu Phe Gly Met Lys Ser Cys Phe
                405                 410                 415

His Glu His Thr Glu Asp Leu Val Ile Arg Ile Thr Met Gly Val Leu
            420                 425                 430

Val Gln Ile Leu Cys Ser Tyr Val Thr Leu Pro Leu Tyr Ala Leu Val
        435                 440                 445

Thr Gln Met Gly Ser Thr Met Lys Pro Thr Ile Phe Asn Glu Arg Val
    450                 455                 460

Ala Thr Ala Leu Arg Asn Trp His His Thr Ala Arg Lys His Ile Lys
465                 470                 475                 480

Gln Asn Arg Gly Ser Met Thr Pro Met Ser Ser Arg Pro Ala Thr Pro
                485                 490                 495

Ser His His Leu Ser Pro Val His Leu Leu Arg His Tyr Arg Ser Glu
            500                 505                 510

Leu Asp Ser Val His Thr Ser Pro Arg Arg Ser Asn Phe Asp Thr Asp
        515                 520                 525

Gln Trp Asp Pro Asp Ser Pro Ser Pro Ser Pro Ser His His Phe His
    530                 535                 540

Arg Arg Pro His Pro Gly Asp Gly Ser Ile Ser Asn His His Arg Asp
545                 550                 555                 560

Val Glu Ala Gly Asp Leu Asp Val Asp Val Glu Ser Pro Gln Pro Asp
                565                 570                 575

Arg Thr Thr Gln Ser Ile Asn Pro Thr Asn Ile Glu His His Glu Ile
            580                 585                 590

Asp Val Gly Ser Asn Glu Phe Ser Phe Asp Arg Arg Val Asp Arg Val
        595                 600                 605


<210> SEQ ID NO 32
<211> LENGTH: 360
<212> TYPE: PRT
<213> ORGANISM: Cucumis sativus

<400> SEQUENCE: 32

Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gly Trp Arg Ala Tyr
65                  70                  75                  80

Leu Trp Leu Pro Phe Val Pro Leu Ile Ile Val Leu Leu Val Gly Thr
                85                  90                  95

Lys Leu Gln Val Ile Ile Thr Lys Met Ala Leu Arg Ile Gln Glu Arg
            100                 105                 110

Gly Glu Val Val Lys Gly Val Pro Val Val Glu Pro Gly Asp Asp Leu
        115                 120                 125

Phe Trp Phe Asn Arg Pro Arg Leu Ile Leu Tyr Leu Ile Asn Phe Val
    130                 135                 140

Leu Phe Gln Asn Ala Phe Gln Leu Ala Phe Phe Ala Trp Thr Trp Lys
```

```
145                 150                 155                 160

Glu Phe Gly Met Lys Ser Cys Phe His Glu His Thr Glu Asp Leu Val
                165                 170                 175

Ile Arg Ile Thr Met Gly Val Leu Val Gln Ile Leu Cys Ser Tyr Val
            180                 185                 190

Thr Leu Pro Leu Tyr Ala Leu Val Thr Gln Met Gly Ser Thr Met Lys
        195                 200                 205

Pro Thr Ile Phe Asn Glu Arg Val Ala Thr Ala Leu Arg Asn Trp His
    210                 215                 220

His Thr Ala Arg Lys His Ile Lys Gln Asn Arg Gly Ser Met Thr Pro
225                 230                 235                 240

Met Ser Ser Arg Pro Ala Thr Pro Ser His His Leu Ser Pro Val His
                245                 250                 255

Leu Leu Arg His Tyr Arg Ser Glu Leu Asp Ser Val His Thr Ser Pro
            260                 265                 270

Arg Arg Ser Asn Phe Asp Thr Asp Gln Trp Asp Pro Asp Ser Pro Ser
        275                 280                 285

Pro Ser Pro Ser His His Phe His Arg Arg Pro His Pro Gly Asp Gly
    290                 295                 300

Ser Ile Ser Asn His His Arg Asp Val Glu Ala Gly Asp Leu Asp Val
305                 310                 315                 320

Asp Val Glu Ser Pro Gln Pro Asp Arg Thr Thr Gln Ser Ile Asn Pro
                325                 330                 335

Thr Asn Ile Glu His His Glu Ile Asp Val Gly Ser Asn Glu Phe Ser
            340                 345                 350

Phe Asp Arg Arg Val Asp Arg Val
        355                 360


<210> SEQ ID NO 33
<211> LENGTH: 593
<212> TYPE: PRT
<213> ORGANISM: Cucumis sativus

<400> SEQUENCE: 33

Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gln Ser Leu Ile Thr
65                  70                  75                  80

Asn Val Cys Ile Pro Pro Asp Val Ala Ala Thr Trp His Pro Cys Ser
                85                  90                  95

Pro Gln Arg Glu Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160
```

```
His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asn Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495

Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
```

```
        580                 585                 590

Val


<210> SEQ ID NO 34
<211> LENGTH: 593
<212> TYPE: PRT
<213> ORGANISM: Cucumis sativus

<400> SEQUENCE: 34

Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Leu Thr Val Gly Gln Ser Leu Ile Thr
65                  70                  75                  80

Asn Val Cys Ile Pro Pro Asp Val Ala Ala Thr Trp His Pro Cys Ser
                85                  90                  95

Pro Gln Arg Glu Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160

His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asx Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
```

-continued

```
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495

Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
            580                 585                 590

Val
```